United States Patent
Zhang et al.

(10) Patent No.: US 8,916,687 B2
(45) Date of Patent: Dec. 23, 2014

(54) INSECTICIDAL PROTEIN, GENE ENCODING THE SAME AND USES THEREOF

(71) Applicants: Beijing Green Agrosino Plant Protection Technology Co., Ltd., Beijing (CN); Beijing Daebeinong Technology Group Co., Ltd., Beijing (CN); Beijing Daebeinong Technology Group Co., Ltd., Biotech Center, Beijing (CN)

(72) Inventors: Aihong Zhang, Beijing (CN); Jie Pang, Beijing (CN); Ruiqi Niu, Beijing (CN); Lihong Niu, Beijing (CN); Na Wang, Beijing (CN); Jincun Huang, Beijing (CN); Yujie Qi, Beijing (CN)

(73) Assignees: Beijing Green Agrosino Plant Protection Technology Co., Ltd., Beijing (CN); Beijing Dabeinong Technology Group Co., Ltd., Biotech Center, Beijing (CN); Beijing Dabeinong Technology Group Co., Ltd., Beijing (CN)

( * ) Notice: Subject to any disclaimer, the term of this patent is extended or adjusted under 35 U.S.C. 154(b) by 0 days.

(21) Appl. No.: 13/846,510

(22) Filed: Mar. 18, 2013

(65) Prior Publication Data
US 2014/0037608 A1 Feb. 6, 2014

(30) Foreign Application Priority Data
Aug. 2, 2012 (CN) .......................... 2010 1 0273515

(51) Int. Cl.
| | | |
|---|---|---|
| *A01N 37/44* | (2006.01) | |
| *A01N 63/00* | (2006.01) | |
| *C07K 14/325* | (2006.01) | |
| *C12N 15/09* | (2006.01) | |
| *A01N 37/46* | (2006.01) | |
| *A01N 63/02* | (2006.01) | |
| *C12N 15/82* | (2006.01) | |
| *A01H 5/00* | (2006.01) | |
| *A01K 67/033* | (2006.01) | |
| *A01N 47/44* | (2006.01) | |
| *A01P 7/04* | (2006.01) | |

(52) U.S. Cl.
CPC ................ *A01N 37/44* (2013.01); *A01N 37/46* (2013.01); *A01N 63/02* (2013.01); *C12N 15/8286* (2013.01); *C07K 14/325* (2013.01); *A01N 63/00* (2013.01)
USPC .......................... 530/350; 424/246.1; 424/405

(58) Field of Classification Search
CPC ....... A01N 37/46; A01N 63/02; A01N 37/44; A01N 63/00; A01N 47/44; A01N 51/00; C07K 14/325; C12N 15/8286; C12N 15/09; C12N 1/19; C12N 1/21; C12N 15/32; C12N 15/63; C12N 15/82; C12N 15/84; C12N 5/10; C12N 7/01; C12N 15/8279; C12P 21/02; A01P 7/04; A01H 5/00; A01K 67/33
See application file for complete search history.

(56) References Cited

FOREIGN PATENT DOCUMENTS

CN 10279618 A 11/2012

OTHER PUBLICATIONS

Accession No. Q45737 UniProtKB/TrEMBL (accessed at URL uniprot.org/uniprot/Q45737 on Dec. 26, 2013, sequence version of Nov. 1, 1996).*
Dardenne et al., "Nucleotide sequence and decduced amino acid sequence of crylA(c) gene variant from *Bacillus thuringiensis*," Nucl. Ac. Res. 18:5546 (1990).*
Xue et al., "Cloning and characterization of a novel Cry1A toxin from *Bacillus thuringiensis* with high toxicity to the Asian corn borer and other lepidopteran insects," FEMS Micro. Lett. 280:95-101 (2008).*
Brian C. Cunningham et al., "High-Resolution Epitope Mapping of hGH-Receptor Interactions by Alanine-Scanning Mutagenesis" Science; Jun. 2, 1989, vol. 244, No. 4908 ; pp. 1081-1085.
Abraham M. De Vos et al., "Human Growth Hormone and Extracellular Domain of Its Receptor: Crystal Structure of the Complex" Science, Jan. 17, 1992, vol. 255, No. 5042, pp. 306-312.
Lorna J. Smith et al., "Human Interleukin 4—The Solution Structure of a Four-helix Bundle Protein" Journal of Molecular Biology, (1992) 224, pp. 899-904.
Chinese First Examination Report of corresponding China Application No. 201210273515.X, dated Jun. 3, 2013.

* cited by examiner

*Primary Examiner* — Christina Bradley
*Assistant Examiner* — Kristina M Hellman
(74) *Attorney, Agent, or Firm* — J.C. Patents

(57) ABSTRACT

The invention relates to an insecticidal protein, its gene encoding and the uses thereof. The protein comprises: (a) a protein consisting of an amino acid sequence shown by SEQ ID NO:2; or (b) a protein derived from (a) consisting of an amino acid sequence by substitution, deletion, or addition of one or more amino acid residues of the amino acid sequences in (a), and having insecticidal activity; or (c) a protein generated by the expression of nucleic acid molecules containing a nucleotide sequence of SEQ ID NO:1; or (d) a protein generated by the expression of nucleic acid molecules containing a complementary sequence that hybridized with SEQ ID NO:1 under stringent conditions; or (e) a protein generated by the expression of nucleic acid molecules that contain nucleotide sequences isocoding with the nucleotide sequences in (d). The insecticidal protein of the invention has high expression level and strong toxicity against pests.

6 Claims, 4 Drawing Sheets

CK            Known Sequence            PIC9-02

CK            Known Sequence            PIC9-02

ND CROSS-REFERENCE TO RELATED
APPLICATIONS

This application claims the priority benefits of Chinese application No. 201210273515.X filed on Aug. 2, 2012. The content of the prior application is hereby incorporated by reference in its entirety.

TECHNICAL FIELD

The invention relates to an insecticidal protein, its gene encoding and uses thereof, more particularly relates to a modified PIC9 insecticidal protein, its gene encoding of the insecticidal protein and uses thereof.

BACKGROUND

Plant pests are a major factor for the loss of crops, resulting in tremendous economic loss of farmers and even affecting the living conditions of local people. Broad-spectrum chemical insecticides and biotic insecticides are often used by people to prevent and control plant pests. However, there are limits for them to be used in practical application: chemical insecticides will lead to environmental contamination and the appearance of drug-resistant insects; and biotic insecticides are easily degraded in environment and need to be applied repeatedly during production, which dramatically increases the production cost.

To address the limitations of chemical insecticides and biotic insecticides in practical application, scientists have found, based on researches, that some insect-resistant transgenic plants can be obtained by transferring insect-resistant gene of encoding insecticidal protein into plants, to prevent and control plant pests. PIC9 insecticidal protein is one of the insecticidal proteins, produced by *Bacillus thuringiensis* sbusp. *kurstaki*, B.t.k. PIC9 is a parasporal insoluble crystal protein.

PIC9 protein is ingested into the mesenteron of insects, and the toxalbumin protoxin is dissolved in alkaline pH environment of insect mesenteron. Protein N-terminal and C-terminal are digested by alkaline proteinase and the protoxin is converted into active fragments. These active fragments are bounded to receptors on the upper surface of epithelial membrane of insect mesenteron, and inserted into the intestine membrane, which results in cell membrane perforation lesions, destroy of the change of osmotic pressure and the pH balance inside and outside cell membrane, and disturbance of the digestion process of insects and finally leading to their death.

There is severe grain loss every year by plant pests, such as maize borer, *agrotis* ypsilon, maize armyworm, or cotton bollworm. So far, there are no reports about the expression level and toxicity of PIC9 insecticidal protein in plants.

SUMMARY

The object of the invention is to provide an insecticidal protein, its gene encoding and uses thereof, wherein the PIC9 insecticidal protein has high expression level and strong toxicity in plant, especially in maize.

To achieve the above object, the invention provides an insecticidal protein, comprising:

(a) a protein consisting of an amino acid sequence shown by SEQ ID NO:2; or (b) a protein derived from (a) consisting of an amino acid sequence by substitution, deletion or addition of one or more amino acid residues of the amino acid sequences in (a), and has insecticidal activity; or (c) a protein generated by the expression of nucleic acid molecules containing a nucleotide sequence of SEQ ID NO:1; or (d) a protein generated by the expression of nucleic acid molecules containing nucleotide sequences, wherein the nucleotide sequences have a complementary sequences that hybridized with SEQ ID NO:1 under stringent conditions; or (e) a protein generated by the expression of nucleic acid molecules containing nucleotide sequences, wherein the nucleotide sequences are isocoding with the nucleotide sequences in (d).

The stringent conditions may be that the hybridization is performed in 6×SSC (sodium citrate), 0.5% SDS (sodium dodecyl sulfate) solution at 65° C., and membrane is then washed once with 2×SSC, 0.1% SDS and 1×SSC, 0.1% SDS, respectively.

To achieve the above object, the invention provides an insecticidal gene, comprising:

(a) nucleotide sequences encoding the protein consisting of an amino acid sequence shown by SEQ ID NO:2; or (b) nucleotide sequences encoding amino acid sequences, wherein the amino acid sequences are the proteins derived from (a) by substitution, deletion or addition of one or more amino acid residues of the amino acid sequences in (a), and having insecticidal activity; or (c) nucleotide sequences containing a nucleotide sequence of SEQ ID NO:1; or (d) nucleotide sequences that hybridized with the nucleotide sequences defined by (c) under stringent conditions and encoding the protein having insecticidal activity; or (e) nucleotide sequences isocoding with the nucleotide sequences in (d).

The stringent conditions may be that the hybridization is performed in 6×SSC (sodium citrate), 0.5% SDS (sodium dodecyl sulfate) solution at 65° C., and membrane is then washed once with 2×SSC, 0.1% SDS and 1×SSC, 0.1% SDS, respectively.

To achieve the above object, the invention further provides an expression cassette, which contains effectively connected insecticidal gene under the regulation of regulatory sequences.

To achieve the above object, the invention further provides a recombinant vector containing the expression cassette.

To achieve the above object, the invention further provides a transgenic host organism containing the insecticidal gene, including plant cells, animal cells, bacteria, yeast, baculovirus, nematodes or algae.

Further, the plant is maize, soybean, cotton, rice or wheat.

To achieve the above object, the invention further provides a method for producing insecticidal proteins, comprising:

acquiring the cells of the transgenic host organism;

culturing the cells of the transgenic host organism under conditions that permit producing insecticidal protein; and recovering the insecticidal protein.

To achieve the above object, the invention further provides a method for widening the range of insects target, comprising:

expressing the expression cassette in a plant together with at least one second insecticidal protein of which that the sequence is different from that of the insecticidal protein of the expression cassette.

Further, the second insecticidal protein is Vip-type insecticidal protein, protease inhibitor, agglutinin, α-amylase or peroxidase.

In the invention, the expression of PIC9-02 insecticidal protein in a transgenic plant can be accompanied with the expression of one or more Vip-type insecticidal proteins. This co-expression of more than one insecticidal toxins in the same transgenic plant can be implemented through genetic engineering which makes the plant contain and express the required gene. In addition, the first plant (the first parent) can express PIC9-02 insecticidal protein by means of genetic engineering manipulation, and the second plant (the second parent) can express Vip-type insecticidal protein by means of genetic engineering manipulation. An offspring plant, which expresses all the genes that were introduced in the first parent and the second parent, can be obtained by the hybridization of the first parent and the second parent.

To achieve the above object, the invention further provides a method for producing insect-resistant plant, comprising: introducing the insecticidal gene or the expression cassette or the recombinant vector into a plant.

Preferably, the plant is maize, soybean, cotton, rice or wheat.

To achieve the above object, the invention further provides a method for protecting plant from damage caused by insect pests, comprising: introducing the insecticidal gene or the expression cassette or the recombinant vector into a plant so that the plant after introduction generates enough insecticidal protein for protecting the plant from the damage caused by insect pests.

Preferably, the plant is maize, soybean, cotton, rice or wheat.

To achieve the above object, the invention further provides a method for controlling insect pests, comprising: contacting insect pests with inhibitory amount of the insecticidal protein, or the insect-inhibitory protein encoded by the insecticidal gene.

Preferably, the insect pests are Lepidoptera insect pests.

The introduction of the insecticidal gene or the expression cassette or the recombinant vector into a plant means introducing exogenous DNA into a plant cell in the invention, and the conventional transformation methods include, but not limited to, *agrobacterium*-mediated transformation, micro emission bombardment, direct ingestion of DNA into a protoplast, electroporation or silicon whisker-mediated DNA introduction.

The genomes of the plant, plant tissue or plant cell in the invention mean any genetic material in the plant, plant tissue or plant cell, and include the genomes of nucleus, plastid and mitochondria.

The 'fragment' or 'segment' of the DNA molecules or protein sequences in the invention means a part of involved original DNA or protein sequences (nucleotide or amino acid) or artificially modified forms thereof (e.g. sequence suitable for expression in a plant), and the length of the aforementioned sequences is variable, but is enough for guaranteeing that (encoded) protein is insect toxin.

Substitution, deletion or addition of amino acid sequences in the invention are conventional techniques in this field, and preferably, this amino acid change is: small feature change, namely, conservative amino acid substitution that has no significant effect on the folding of protein and/or activity of the protein; small deletion, typically deletion of about 1-30 amino acids; small extension of amino terminal or carboxyl terminal, for example, one methionine residue is extended at amino terminal; and small connecting peptide, e.g. about 20-25 residues long.

The examples of conservative substitution means the substitution that occurs in the following group of amino acids: alkaline amino acids (such as arginine, lysine and histidine), acidic amino acids (such glutamic acid and aspartic acid), polar amino acids (such as glutamine and asparagine amide), hydrophobic amino acids (such as leucine, isoleucine and valine), aromatic amino acids (such as phenylalanine, tryptophan and tyrosine), and micromolecular amino acids (such as glycine, alanine, serine, threonine and methionine). Those substitutions of amino acids that typically do not change specific activity are well known in this field, and have been described in, for example, *Protein* that was written by N. Neurath and R. L. Hill and published by Academic Press of New York in 1979. The most common interchanges are Ala/Ser, Val/Ile, Asp/Glu, Thu/Ser, Ala/Thr, Ser/Asn, Ala/Val, Ser/Gly, Tyr/Phe, Ala/Pro, Lys/Arg, Asp/Asn, Leu/Ile, Leu/Val, Ala/Glu and Asp/Gly, and their reversal interchanges.

It is apparent for those skilled in this field that, this substitution can occur out of a region that playing an important role in molecular functions, and still generates active polypeptides. For polypeptides in the invention, the amino acid residues that are necessary for the activities of polypeptides and therefore choosen to be not substituted can be identified based upon the methods known in this art, e.g. site-directed mutagenesis or alanine scanning mutagenesis (e.g. see Cunningham and Wells, 1989, Science 244: 1081-1085). The latter technique is that introducing a mutation at every positively charged residue in molecule, and then detecting the insect-resistant activity of the resultant mutation molecules so as to determine amino acid residues that are important for the molecular activity. Substrate-enzyme interaction site can also be determined by analysis of its three-dimensional structure, and such three-dimensional structure can be determined by techniques such as NMR analysis, crystallography or photoaffinity labeling, etc. (for example, see de Vos et al., 1992, Science 255: 306-312; Smith et al., 1992, J. Mol. Biol. 224: 899-904; Wlodaver et al., 1992, FEBS Letters 309: 59-64).

Therefore, amino acid sequences having certain homology with the amino acid sequences shown by Sequence 2 are also included in the invention. These sequences have at least about 40%-50% homology with the sequences in the invention, about 60%, 65% or 70%, and even at least about 75%, 80%, 85%, 90%, 91%, 92%, 93%, 94%, 95%, 96%, 97%, 98%, 99% or more homology. That is to say, the range of sequence homology is at least about 40%-50%, about 60%, 65% or 70%, and even at least about 75%, 80%, 85%, 90%, 91%, 92%, 93%, 94%, 95%, 96%, 97%, 98%, 99% or more.

The nuclear acid molecules or segments thereof in the invention can be hybridized with the insecticidal gene in the invention under stringent conditions. Any conventional nuclear acid hybridization or amplification method can be used to identify the existence of the insecticidal gene according to the invention. Nuclear acid molecules or segments thereof can specifically be hybridized with other nuclear acid molecules under a certain circumstance. In the invention, if two nuclear acid molecules can form an antiparallel double-stranded nuclear acid structures, this means these two nuclear acid molecules can specifically be hybridized with each other. If two nuclear acid molecules show complete complementarity, one of them is called as the "complement" of the other. In the invention, when every nucleotide in one nuclear acid molecule is complementary to the corresponding nucleotide in the other nuclear acid molecule, the two nuclear acid molecules show "complete complementarity". If two nuclear acid molecules can be hybridized with each other with enough stability so that they are annealed and bound with each other under at least conventional "lowly-stringent" conditions, these two nuclear acid molecules are "complement at the lowest". Similarly, if two nuclear acid molecules can be hybridized with each other with enough stability so that they are annealed and bound with each other under conventional "highly-stringent" conditions, the two nuclear acid molecules have "complementarity". Deviation from complete complementarity is allowed only if this deviation does not completely prevent two molecules from forming a double-stranded structure. In order to make one nuclear acid molecule be used as primer or probe, it only need to ensure there is sufficient complementarity on sequence, so that a stable double-stranded structure can be formed under the specific solvent and salinity that are used.

In the invention, sequence that is substantially homologous is a segment of nuclear acid molecule, which can be specifically hybridized with a matched complementary strand of another segment of nuclear acid molecule under highly stringent conditions. There are suitable stringent conditions for promoting DNA hybridization, for example, treating DNA with 6.0×sodium chloride/sodium citrate (SSC) at about 45° C. and then washing it with 2.0×SSC at 50° C., and these conditions are well known for those skilled in this art. For example, salinity in the washing step may be selected from about 2.0×SSC, 50° C. of lowly stringent conditions to about 0.2×SSC, 50° C. of highly stringent conditions. In addition, temperature conditions in the washing step may be rised from about 22° C. room temperature of lowly stringent conditions to about 65° C. of highly stringent conditions. The temperature conditions and salinity both can be changed, or one of them is unchanged while the other is changed. Preferably, the stringent conditions of the invention may be that performing a specific hybridization with SEQ ID NO:1 in 6×SSC, 0.5% SDS solution at 65° C., and the membrane is then washed once with 2×SSC, 0.1% SDS and 1×SSC, 0.1% SDS, respectively.

Therefore, sequences which have insecticidal activity and can be hybridized to the sequence 1 in the invention under stringent conditions are included in the invention. These sequences have at least about 40%-50% homology with the sequences in the invention, about 60%, 65% or 70%, and even at least about 75%, 80%, 85%, 90%, 91%, 92%, 93%, 94%, 95%, 96%, 97%, 98%, 99% or more homology. That is to say, the range of sequence homology is at least about 40%-50%, about 60%, 65% or 70%, and even at least about 75%, 80%, 85%, 90%, 91%, 92%, 93%, 94%, 95%, 96%, 97%, 98%, 99% or more.

When polypeptides encoded by a nuclear acid sequence have the same amino acid sequences as polypeptides encoded by a reference nuclear acid sequence, the nuclear acid sequence and the reference nuclear acid sequence are the "isocoding" as described in the invention.

The regulatory sequences in the invention include, but not limited to, promoters, transit peptides, terminators, enhancers, leader sequences, introns and other regulatory sequences operatively connected to the insecticidal gene.

The promoters are expressible promoters in plant, and the "expressible promoters in plant" are promoters that can ensure, in a plant cell, the expression of coding sequences connected therewith. The expressible promoters in plant may be constitutive promoters. The examples of promoters that guide constitutive expression in plant include, but not limited to, 35S promoter from cauliflower mosaic virus, ubi promoter, promoter of rice GOS2 gene and the like. Alternatively, the expressible promoters in plant may be tissue-specific promoters, namely, having higher level of guiding the expression of coding sequences in some tissues of plant, e.g. in chlorenchyma, than in other tissues of plant (which can be determined by conventional RNA test), e.g. PEP carboxylase promoter. Alternatively, the expressible promoters in plant may be wound-induced promoters. The wound-induced promoters or the promoters guiding the wound-introduced expression pattern indicate that, when a plant is wounded by machine or by insect biting, the expression of coding sequences under the regulation of promoter is significantly improved compared with that under normal growth conditions. The examples of the wound-induced promoters include, but not limited to, promoters of potato and tomato protease suppressor genes (pin I and pin II) and of maize protease suppressor genes (MPI).

The transit peptides (also known as secretion signal sequence or targeting sequence) are used to guide transgenic product to a specific cellular organ or a cellular compartment, and may be heterogenous for receptor protein, for example, using coded chloroplast transit peptide sequence for targeting chloroplast, or using 'KDEL' conservative sequence for targeting endoplasmic reticulum, or using CTPP of barley lectin gene for targeting vacuole.

The leader sequences include, but not limited to, leader sequence of small RNA viruses, such as EMCV leader sequence (5' non-encoding region of encephalomyocarditis virus); leader sequence of potato virus Y group, such as leader sequence of MDMV (maize dwarf mosaic virus); human immune globulin heavy chain binding protein (BiP); untranslated leader sequence (AMV RNA4) of coat protein mRNA of alfalfa mosaic virus; leader sequence of tobacco mosaic virus (TMV).

The enhancers include, but not limited to, cauliflower mosaic virus (CaMV) enhancer, figwort mosaic virus (FMV) enhancer, carnation etched ring virus (CERN) enhancer, cassava vein mosaic virus (CsVMV) enhancer, mirabilis mosaic virus (MMV) enhancer, Cestrum yellow leaf curling virus (CmYLCV) enhancer, cotton leaf curl multan virus (CLCuMV) enhancer, commelina yellow mottle virus (CoYMV) enhancer and peanut chlorotic streak virus (PCLSV) enhancer.

For the application of monocotyledons, the introns include, but not limited to, maize hsp70 intron, maize ubiquitin intron, Adh intron 1, sucrose synthase intron or rice Act1 intron. For the application of dicotyledons, the introns include, but not limited to, CAT-1 intron, pKANNIBAL intron, PIV2 intron and 'Super ubiquitin' intron.

The terminators may be suitable polyadenylation signal sequences that function in plant, including, but not limited to, polyadenylation signal sequences derived from *Agrobacterium tumefaciens* nopaline synthetase (NOS) gene, polyadenylation signal sequences derived from protease inhibitor II (pin II) gene, polyadenylation signal sequences derived from pea ssRUBISCO E9 gene and polyadenylation signal sequences derived from α-tubulin gene.

The 'effective connection' in the invention indicates the linkage of nuclear acid sequences. The linkage enables one sequence to provide functions the connected sequences required. The 'effective connection' in the invention may be the connection between a promoter and an interested sequence, so that transcription of the interested sequence is controlled and regulated by the promoter. When the interested sequence encodes a protein and expression of this protein is desired, the 'effective connection' indicates that: a promoter is connected with the sequence in such a manner that the resultant transcript is highly translated. If the connection between a promoter and a coding sequence is transcript fusion and the expression of coded protein is desired, the connection is such that the first translation initiation codon is the initiation codon of encoding sequence. Alternatively, if the connection between a promoter and a coding sequence is translation fusion and the expression of coded protein is desired, the connection is such that the first translation initiation codon contained in 5' untranslated sequence is connected with the promoter in such a manner that the relation between the resultant translation product and the translation open reading frame that encoding the protein desired is in conformity with the reading frame. The nuclear acid sequences capable of 'effective connection' include, but not limited to: sequences providing the function of gene expression (i.e. gene expression elements, such as promoter, 5' untranslated region, intron, protein coding region, 3' untranslated region, polyadenylation site and/or transcription terminator), sequences providing the function of DNA transfer and/or integration function (i.e. T-DNA border sequence, site-specific recombinase recognition site, integrase recognition site), sequences providing the selective function (i.e. antibiotic-resistant marker, biosynthetic gene), sequences providing the function of scoring marker, sequence assisting the sequence operation in vitro or in vivo (i.e. polylinker sequence, site-specific recombinant sequence), and sequences providing the function of replication (i.e. replication origin of bacteria, autonomous replication sequence, centromeric sequence).

The 'insecticidal' in the invention indicates toxicity against crop pests. More particularly, target insects are pests, for example, but not limited to, most of the Lepidoptera pests, such as maize borer, *agrotis* ypsilon, maize armyworm, cotton bollworm orrice stem borer etc.

In the invention, the insecticidal protein has PIC9-02 amino acid sequences, shown by SEQ ID NO: 2 in the sequence list. The insecticidal gene has PIC9-02 nucleotide sequence, shown by SEQ ID NO: 1. When the insecticidal gene, especially maize-transformed DNA sequence, is used for plant, besides the encoding region of a protein encoded by PIC9-02 nucleotide sequence, it can comprises other elements, such as encoding region of transit peptides, and encoding region of selectively marked protein or encoding region of protein imparting resistance to herbicides.

The PIC9-02 insecticidal protein in the invention is toxic to most of the Lepidoptera pests causing damage to maize. The plant described in the invention, especially maize, contains exogenous DNA in their genome, and the exogenous DNA contains PIC9-02 nucleotide sequences, so that the plant is protected from pests by expressing the suppressive quantity of this protein. The suppressive quantity refers to lethal dosage or sub-lethal dosage. Simultaneously, the plant should be normal in morphology, and can be cultured according to a conventional method for the purpose of product consumption and/or production. In addition, the plant can substantially eliminate the need for chemical or biotic insecticides (the chemical or biotic insecticides are insecticides which are directed against insects that targeted by PIC9-02 nucleotide sequence-coded protein).

The expression level of insecticidal crystal protein (ICP) in plant materials can be determined by multiple methods described in this art, for example, by quantifying mRNA, which is generated in tissue and encodes the insecticidal protein, via using a specific primer, or by specifically determining the quantity of the generated insecticidal protein directly.

The insecticidal effect of ICP in plant can be determined by means of different tests. The target insects in the invention mainly are Lepidoptera insects, more particularly, Asian corn borer, *pseudaletia separata*, cotton bollworm, rice stem borer or pink stem borer, etc.

In addition, the expression cassette containing the insecticidal gene (PIC9-02 gene) sequences of the invention can also be expressed in plant together with at least one gene encoding herbicide-resistant protein, so as to obtain a transgenic plant having both high insecticidal activity and herbicide resistance. The herbicide-resistant genes include, but not limited to, glufosinate-resistant genes (e.g. bar gene, pat gene), phenmedipham-resistant genes (e.g. pmph gene), glyphosate-resistant genes (e.g. EPSPS gene), bromoxynil-resistant genes, sulfonylurea-resistant genes, herbicide dalapon-resistant genes, and cyanamide-resistant genes or glutamine synthetase inhibitor-resistant genes (e.g. PPT-resistant gene).

The invention provides an insecticidal protein, a gene encoding the insecticidal protein and use thereof. The insecticidal protein has the following advantages:

1. Strong toxicity. The insecticidal protein PIC9-02 of the invention has strong insecticidal toxicity, especially against Lepidoptera pests which cause damage to maize.

2. High expression level. The insecticidal protein PIC9-02 of the invention, which adopts preferred codons of maize, is completely in conformity with the features of maize gene, so that the insecticidal gene of the invention is particularly suitable for expression in monocotyledons, especially in maize, with high level of expression and good stability.

The technical solution of the invention will be further described in detail below with reference to the accompanying drawings and examples.

DETAILED DESCRIPTION

Figure 1:
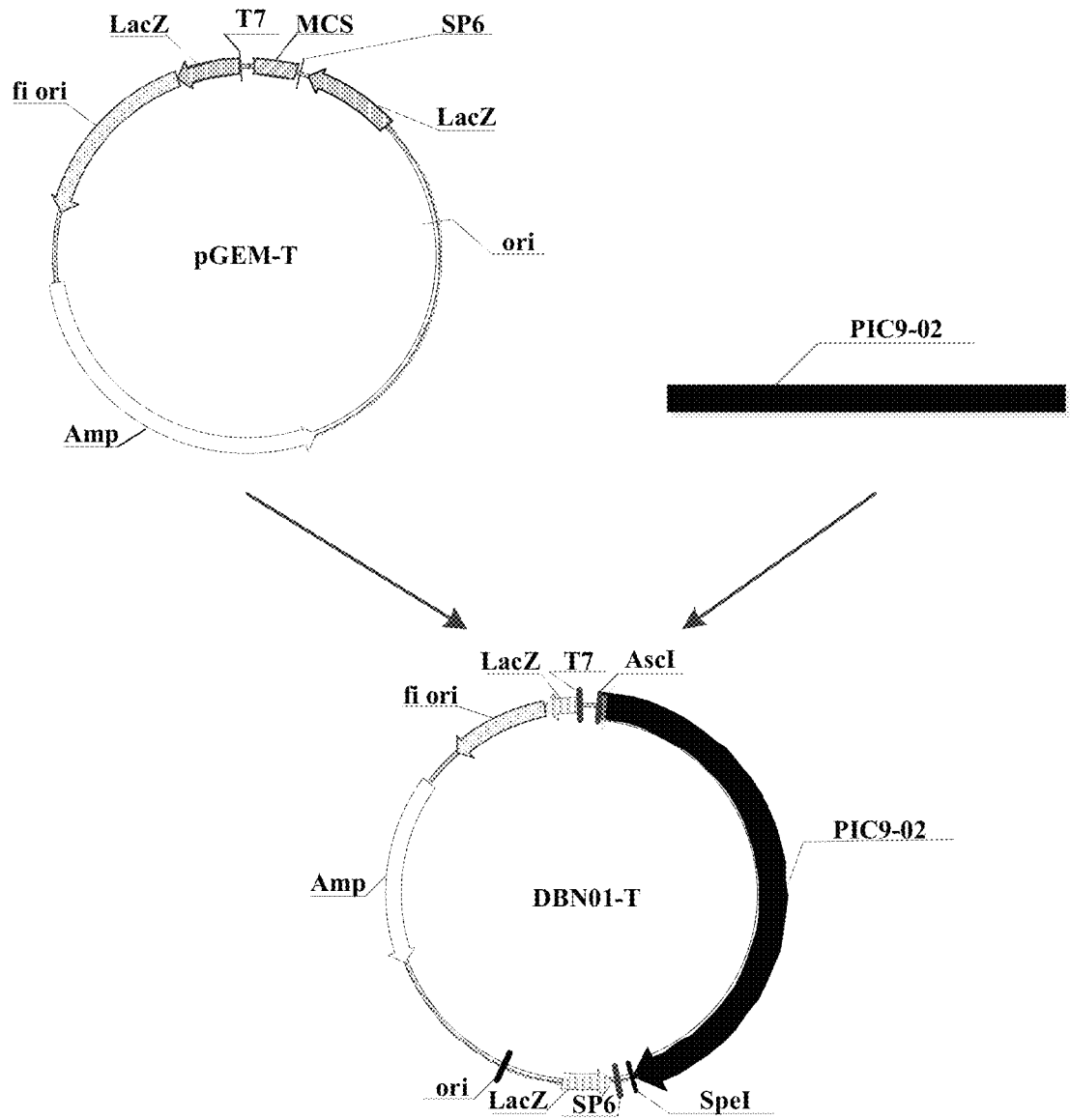
FIG. 1 is a construction flow chart of recombinant cloning vector DBN01-T containing PIC9-02 nucleotide sequences.

The technical solution of the insecticidal protein, the gene encoding the insecticidal protein and use thereof in the invention will be further described below with reference to the examples.

Example 1

Acquisition and Synthesis of PIC9-02 Gene Sequence

1. Acquisition of PIC9-02 Gene Sequence

The amino acid sequence (699 amino acids) of PIC9-02 insecticidal protein is shown by SEQ ID NO:2 in the sequence list; A nucleotide sequence (2100 nucleotides), which codes the amino acid sequence (699 amino acids) corresponding to the PIC9-02 insecticidal protein, is acquired according to the preferred codons of maize, shown by SEQ ID NO:1 in the sequence list. The use of the preferred codons of maize can be seen on the internet.

2. Synthesis of PIC9-02 Nucleotide Sequence

The PIC9-02 nucleotide sequence (shown by SEQ ID NO:1 in the sequence list) is synthesized by Nanjing Genscript Biotechnology Co., Ltd.; the 5' terminal of the synthesized PIC9-02 nucleotide sequence (SEQ ID NO:1) is further connected with AscI enzyme cutting site, and the 3' terminal of the PIC9-02 nucleotide sequence (SEQ ID NO:1) is further connected with SpeI enzyme cutting site.

Meanwhile, synthesis of PIC9-02 substituted nucleotide sequence (shown by SEQ ID NO:3 in the sequence list) is characterized in that Cys at the position 674 of the PIC9-02 amino acid sequence (shown by SEQ ID NO:2 in the sequence list) is replaced by Tyr; the 5' terminal of the synthesized PIC9-02 substituted nucleotide sequence (SEQ ID NO:3) is further connected with AscI enzyme cutting site, and the 3' terminal of the PIC9-02 substituted nucleotide sequence (SEQ ID NO:3) is further connected with SpeI enzyme cutting site.

Meanwhile, synthesis of PIC9-02 deleted nucleotide sequence (shown by SEQ ID NO:4 in the sequence list) is characterized in that amino acids at positions 641 to 650 of the PIC9-02 amino acid sequence (shown by SEQ ID NO:2 in the sequence list) are deleted; the 5' terminal of the synthesized PIC9-02 deleted nucleotide sequence (SEQ ID NO:4) is further connected with AscI enzyme cutting site, and the 3' terminal of the PIC9-02 deleted nucleotide sequence (SEQ ID NO:4) is further connected with SpeI enzyme cutting site.

Meanwhile, synthesis of PIC9-02 added nucleotide sequence (shown by SEQ ID NO:5 in the sequence list) is characterized in that 5 amino acids, Asp, Glu, Arg, Asn and Leu, are added behind position 699 of the PIC9-02 amino acid sequence (shown by SEQ ID NO:2 in the sequence list); the 5' terminal of the synthesized PIC9-02 added nucleotide sequence (SEQ ID NO:5) is further connected with AscI enzyme cutting site, and the 3' terminal of the PIC9-02 added nucleotide sequence (SEQ ID NO:5) is further connected with SpeI enzyme cutting site.

Example 2

Construction of Recombinant Expression Vector and Transformation of Recombinant Expression Vector into *Agrobacterium*

1. Construction of Recombinant Cloning Vector DBN01-T Containing PIC9-02 Nucleotide sequence The synthesized PIC9-02 nucleotide sequence is connected into cloning vector pGEM-T (Promega, Madison, USA, CAT: A3600) according to the instruction of pGEM-T vector product from Promega company, thus recombinant cloning vector DBN01-T is obtained, and the construction flow is shown in FIG. 1 (wherein, Amp represents penbritin-resistant gene; f1 represents the replacation origin of phage f1; LacZ is LacZ initiation codon; SP6 is SP6 RNA polymerase promoter; T7 is T7 RNA polymerase promoter; PIC9-02 is PIC9-02 nucleotide sequence (SEQ ID NO: 1); and MCS is multi-cloning site).

Then, the recombinant cloning vector DBN01-T is transformed into *E. coli* T1 competent cell (Transgen, Beijing, China; Cat. No: CD501) by heat shock under the following conditions: putting 50 μl *E. coli* T1 competent cell and 10 μl plasmid DNA (recombinant cloning vector DBN01-T) in water bath at 42° C. for 30 seconds; then putting them in water bath at 37° C. for 1 hour (on a shaking bed at a speed of 100 rpm), growing them overnight on an LB plate (10 g/L tryptone, 5 g/L yeast extract, 10 g/L NaCl, 15 g/L agar, pH is regulated to 7.5 by NaOH) containing penbritin (100 mg/L) and coated with X-gal (5-bromo-4-chloro-3-indole-beta-D-galactoside) on the surface. Picking white colonies and then culturing them overnight in an LB liquid medium (10 g/L tryptone, 5 g/L yeast extract, 10 g/L NaCl, 100 mg/L penbritin, pH is regulated to 7.5 by NaOH) at 37° C. Extracting plasmids from the white colonies by alkaline process: centrifuging the bacterial liquid at 12000 rpm for 1 minute, removing supernatant, suspending deposited bacteria with 100 μl pre-cooled icy solution I (25 mM Tris-Hcl, 10 mM EDTA (ethylene diamine tetraacetic acid), 50 mM glucose, pH 8.0); adding 150 μl newly-prepared solution II (0.2M NaoH, 1% SDS (sodium dodecyl sulfate)), reversing the tube for four times to mix the substances in the tube, and putting the tube on ice for 3 to 5 minutes; adding 150 μl icy solution III (4M potassium acetate, 2M acetic acid), fully and uniformly mixturing the substances in the tube at once, and putting the tube on ice for 5 to 10 minutes; centrifuging the tube at 12000 mm for 5 minutes at 4° C., adding absolute ethanol of 2×volume to supernatant, uniformly mixed, and then letting the mixture stand for 5 minutes at room temperature; centrifuging the mixture at 12000 rpm for 5 minutes at 4° C. to remove the supernatant, washing the deposit with ethanol of 70 wt % and then drying the deposit in the air; adding 30 μl TE (10 mM Tris-HCL, 1 mM EDTA, PH 8.0) containing Rnase (20 μg/ml) to dissolve the deposit; putting them in water bath at 37° C. for 30 minutes to digest RNA; and preserving them at −20° C. for future use.

Positive colonies are confirmed by sequencing after the extracted plasmids are subjected to AscI and SpeI enzyme cleave identification, and the result shows that the PIC9-02 nucleotide sequence, inserted into the recombinant cloning vector DBN01-T, is the nucleotide sequence shown by SEQ ID NO:1 in the sequence list, indicating that the PIC9-02 nucleotide sequence is correctly inserted.

According to the method for constructing recombinant cloning vector DBN01-T, the synthesized PIC9-02 substituted nucleotide sequence is connected into cloning vector pGEM-T to obtain recombinant cloning vector DBN02-T, wherein miPIC9-02 is PIC9-02 substituted nucleotide sequence (SEQ ID NO:3). The correct substitution of the PIC9-02 substituted nucleotide sequence in recombinant cloning vector DBN02-T is identified through enzyme cleave and sequencing.

According to the method for constructing recombinant cloning vector DBN01-T, the synthesized PIC9-02 deleted nucleotide sequence is connected into cloning vector pGEM-T to obtain recombinant cloning vector DBN03-T, wherein mdPIC9-02 is PIC9-02 deleted nucleotide sequence (SEQ ID NO:4). The correct insertion of the PIC9-02 deleted nucleotide sequence in recombinant cloning vector DBN03-T is identified through enzyme cleave and sequencing.

According to the method for constructing recombinant cloning vector DBN01-T, the synthesized PIC9-02 added nucleotide sequence is connected into cloning vector pGEM-T to acquire recombinant cloning vector DBN04-T, wherein maPIC9-02 is PIC9-02 added nucleotide sequence (SEQ ID NO:5). The correct insertion of the PIC9-02 added nucleotide sequence in recombinant cloning vector DBN04-T is identified through enzyme cleave and sequencing.

Figure 2:
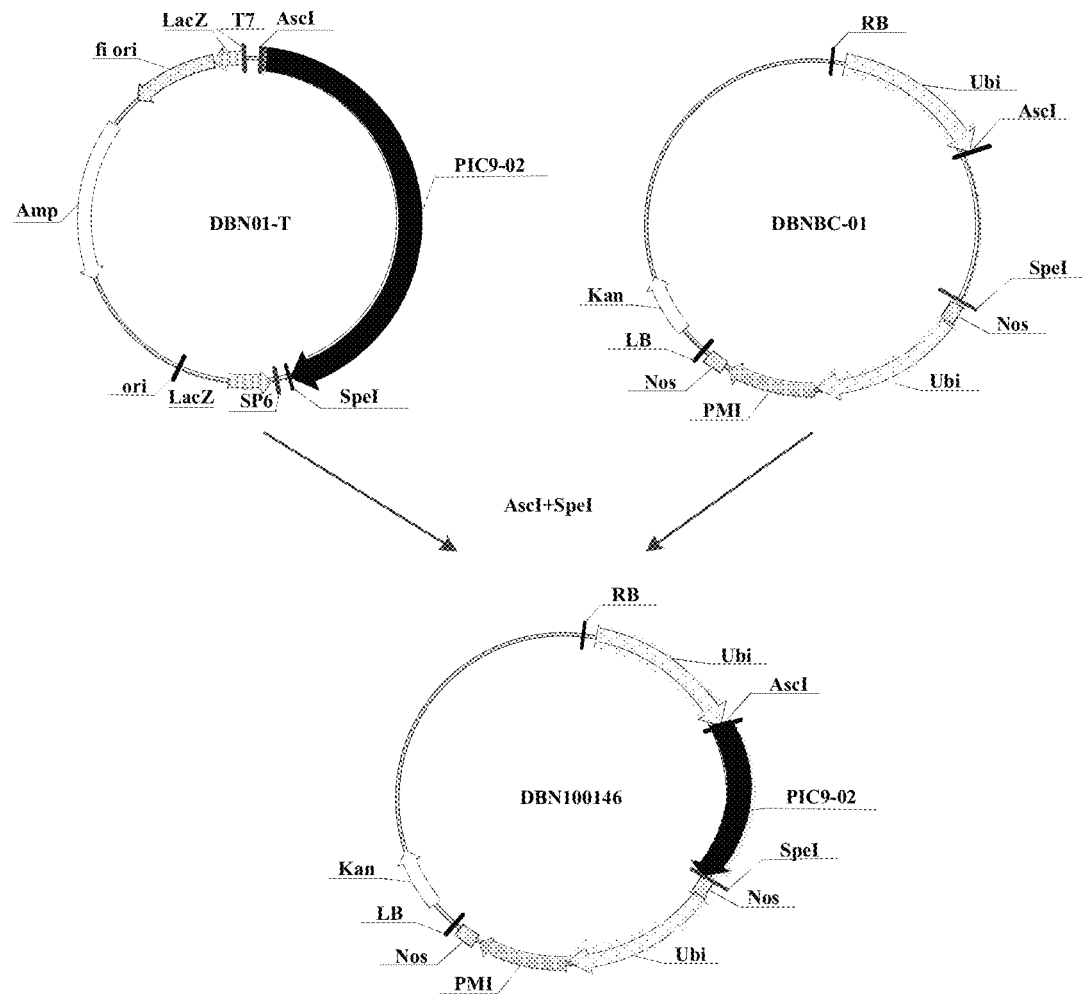
FIG. 2 is a construction flow chart of recombinant expression vector DBN100146 containing PIC9-02 nucleotide sequences.

2. Construction of Recombinant Expression Vector DBN100146 Containing PIC9-02 Nucleotide Sequence Recombinant cloning vector DBN01-T and expression vector DBNBC-01 (vector backbone: pCAMBIA2301 (which can be offered by CAMBIA institution)) are cut by restriction endonucleases AscI and SpeI, respectively. The PIC9-02 nucleotide sequence segments that are cut off are inserted between the AscI site and the SpeI site of expression vector DBNBC-01. As the construction of vector by conventional enzyme cutting methods is acknowledged by those skilled in this art, the AscI and SpeI enzyme cutting sites in expression vector DBNBC-01 are also introduced by conventional enzyme cutting method so as to construct recombinant expression vector DBN100146. The construction flow is shown in FIG. 2 (Kan: kanamycin gene; RB: right border; Ubi: maize ubiquitin gene promoter (SEQ ID NO: 6); PIC9-02: PIC9-02 nucleotide sequence (SEQ ID NO: 1); Nos: nopaline synthetase terminator (SEQ ID NO: 7); PMI: phosphomannose isomerase gene (SEQ ID NO: 8); and LB: left border).

The recombinant expression vector DBN100146 is transformed into E. coli T1 competent cell by heat shock under the following conditions: putting 50 μl E. coli T1 competent cell and 10 μl plasmid DNA (recombinant expression vector DBN100146) in water bath at 42° C. for 30 seconds; then putting them in water bath at 37° C. for 1 hour (on a shaking bed at 100 rpm); then culturing them on an LB solid plate (10 g/L tryptone, 5 g/L yeast extract, 10 g/L NaCl, 15 g/L agar, pH is regulated to 7.5 by NaOH) containing 50 mg/L kanamycin for 12 hours at 37° C.; piching white colonies and then culturing them overnight in an LB liquid medium (10 g/L tryptone, 5 g/L yeast extract, 10 g/L NaCl, 50 mg/L kanamycin, pH is regulated to 7.5 by NaOH) at 37° C. Plasmids of the white colonies are extracted by alkaline process. The plasmids extracted are identified by restriction endonucleases AscI and SpeI, and positive colonies are verified by sequencing. The result shows that the nucleotide sequence of the recombinant expression vector DBN100146 between the AscI site and the SpeI site is the nucleotide sequence shown by SEQ ID NO: 1 in the sequence list, namely, the PIC9-02 nucleotide sequence.

According to the method for constructing recombinant expression vector DBN100146 as described above, the PIC9-02 substituted nucleotide sequence cut from the recombinant cloning vector DBN02-T by AscI and SpeI is inserted into expression vector DBNBC-01 to acquire recombinant expression vector DBN100146-i. Through enzyme cleave and sequencing identification, the recombinant expression vector DBN100146-i between the AscI site and the SpeI site is the PIC9-02 substituted nucleotide sequence.

According to the method for constructing recombinant expression vector DBN100146 as described above, the PIC9-02 deleted nucleotide sequence cut from the recombinant cloning vector DBN03-T by AscI and SpeI is inserted into expression vector DBNBC-01 to acquire recombinant expression vector DBN100146-d. Through enzyme cleave and sequencing identification, the recombinant expression vector DBN100146-d between the AscI site and the SpeI site is the PIC9-02 deleted nucleotide sequence.

According to the method for constructing recombinant expression vector DBN100146 as described above, the PIC9-02 added nucleotide sequence cut from the recombinant cloning vector DBN04-T by AscI and SpeI is inserted into expression vector DBNBC-01 to acquire recombinant expression vector DBN100146-a. Through enzyme cleave and sequencing identification, the recombinant expression vector DBN100146-a between the AscI site and the SpeI site is the PIC9-02 added nucleotide sequence.

3. Construction of Recombinant Expression Vector DBN100146R Containing Known Sequence (Positive Control)

According to the method for constructing recombinant cloning vector DBN01-T containing PIC9-02 nucleotide sequence, as described in part 1 of example 2 of the invention, recombinant cloning vector DBN01R-T containing known sequence (SEQ ID NO:9) is constructed by using the known sequence. Sequencing verification is carried out on positive colonies, and the result shows that the known sequence inserted into the recombinant cloning vector DBN01R-T is the nucleotide sequence shown by SEQ ID NO: 9 in the sequence list, indicating that the known sequence is correctly inserted.

Figure 3:
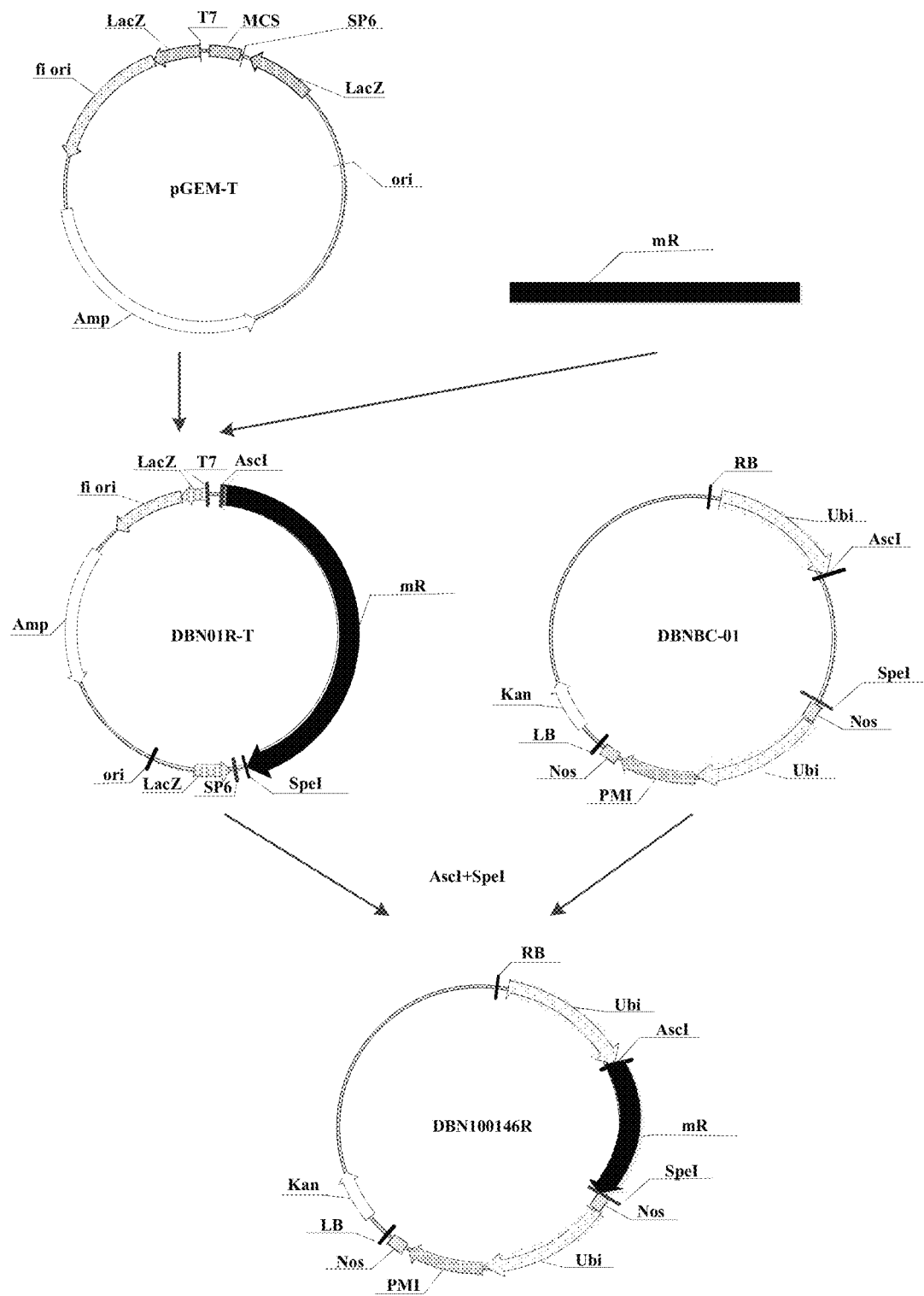
FIG. 3 is a construction flow chart of recombinant expression vector DBN100146R containing known sequences; the known sequence is SEQ ID NO:9.

According to the method for constructing recombinant expression vector DBN100146 containing PIC9-02 nucleotide sequence, as described in part 2 of example 2 of the invention, recombinant expression vector DBN100146R containing a known sequence is constructed using the known sequence, and the construction flow is shown in FIG. 3 (vector backbone: pCAMBIA2301 (which can be provided by CAMBIA institution); Kan: kanamycin gene; RB: right border; Ubi: maize ubiquitin gene promoter (SEQ ID NO:6); mR: known sequence (SEQ ID NO: 9); Nos: nopaline synthetase terminator (SEQ ID NO:7); PMI: phosphomannose isomerase gene (SEQ ID NO:8); and LB: left border). Sequencing verification is carried out on positive colonies, and the result shows that the known sequence inserted into the recombinant expression vector DBN100146R is the nucleotide sequence shown by SEQ ID NO: 9 in the sequence list, indicating that the known sequence is correctly inserted.

4. Transformation of Recombinant Expression Vector into Agrobacterium

The recombinant expression vectors DBN100146, DBN100146-i, DBN100146-d, DBN100146-a, and DBN100146R (known sequence), which have been correctly constructed, are transformed into agrobacterium LBA4404 (Invitrgen, Chicago, USA; Cat. No: 18313-015) by a liquid nitrogen method, and the transformation conditions are as follows: putting 100<4, agrobacterium LBA4404 and 3 μL plasmid DNA (recombinant expression vector) in liquid nitrogen for 10 minutes and then putting them in water bath at 37° C. for 10 minutes; inoculating the transformed agrobacterium LBA4404 in an LB test tube and culturing it for 2 hours at 28° C. at 200 rpm, and then coating it on an LB plate containing 50 mg/L rifampicin and 100 mg/L kanamycin until positive monoclone appears, picking and culturing the positive monoclone and extracting the plasmids therefrom. Enzyme cleave identification is carried out on the positive monoclone after it is cut by restriction endonucleases BgIII and AatII; the result shows that the structures of recombinant expression vectors DBN100146, DBN100146-i, DBN100146-d, DBN100146-a, and DBN100146R (known sequence) are completely correct.

Example 3

Acquisition and Verification of PIC9-02 Nucleotide Sequence-Transferred Maize Plant 1. Acquisition of PIC9-02 Nucleotide Sequence-Transferred Maize Plant The immature embryos of maize strain Z31 cultured under sterile conditions and the agrobacterium mentioned in part 4 of example 2 are co-cultured according to the commonly used agrobacterium infection method, so as to transfer the T-DNAs (including promoter sequence of maize Ubiquitin gene, PIC9-02 nucleotide sequence, PIC9-02 substituted nucleotide sequence, PIC9-02 deleted nucleotide sequence, PIC9-02 added nucleotide sequence, known sequence, PMI gene and Nos terminator sequence) of the recombinant expression vectors DBN100146, DBN100146-i, DBN100146-d, DBN100146-a, and DBN100146R (known sequence) constructed in part 2 and part 3 of Example 2 into maize genome, so that PIC9-02 nucleotide sequence-transferred maize plant, PIC9-02 substituted nucleotide sequence-transferred maize plant, PIC9-02 deleted nucleotide sequence-transferred maize plant, PIC9-02 added nucleotide sequence-transferred maize plant and known sequence-transferred maize plant are acquired (positive control); meanwhile, wild-type maize plant is used as negative control.

In brief, for *agrobacterium*-mediated maize transformation, immature embryos are separated from maize and contact *agrobacterium* suspension, wherein *agrobacterium* can transfer PIC9-02 nucleotide sequence to at least one cell of one of the immature embryos (Step 1: infestation step), and the promoter is operatively connected with the PIC9-02 nucleotide sequence. In this step, the immature embryos are preferably immersed in *agrobacterium* suspension ($OD_{660}$=0.4-0.6, infestation medium (4.3 g/L MS salt, MS vitamin, 300 mg/L casein, 68.5 g/L sucrose, 36 g/L glucose, 40 mg/L acetosyringone (AS), 1 mg/L 2,4-Dichlorophenoxyacetic acid (2,4-D), and pH 5.3) so as to initiate inoculation. The immature embryos and the *agrobacterium* are co-cultured for a period of time (3 days) (step 2: co-culture step). Preferably, the immature embryos, after the infestation step, are cultured on a solid medium (4.3 g/L MS salt, MS vitamin, 300 mg/L casein, 20 g/L sucrose, 10 g/L glucose, 100 mg/L acetosyringone (AS), 1 mg/L 2,4-Dichlorophenoxyacetic acid (2,4-D), 8 g/L agar, and pH 5.8). There may be an optional 'recovery' step after this co-culture step. In the 'recovery' step, there is at least one antibiotic (cephalosporin) known to suppress the growth of *agrobacterium* in the medium (4.3 g/L MS salt, MS vitamin, 300 mg/L casein, 30 g/L sucrose, 1 mg/L 2,4-Dichlorophenoxyacetic acid (2,4-D), 8 g/L agar, and pH 5.8), and there is no selector of plant transformant added (step 3: recovery step). Preferably, the immature embryos are cultured on the solid medium containing antibiotic but not selector so as to eliminate *agrobacterium* and provide a period of time for recovery of the infected cells. Then, the inoculated immature embryos are cultured on the medium containing selector (mannose) and the growing transformed callus is choosed (step 4: choosing step). Preferably, the immature embryos are cultured on a selector-containing screening solid medium (4.3 g/L MS salt, MS vitamin, 300 mg/L casein, 5 g/L sucrose, 12.5 g/L mannose, 1 mg/L 2,4-Dichlorophenoxyacetic acid (2,4-D), 8 g/L agar, and pH 5.8) to result in the selective growth of the transformed cells. Afterwards, the callus is regenerated to be a plant (step 5: regeneration step). Preferably, the callus, which grows on a selector-containing medium, is cultured on solid mediums (MS differentiation medium and MS rooting medium) to regenerate a plant.

Resistant callus that obtained by screening is transferred to the MS differentiation medium (4.3 g/L MS salt, MS vitamin, 300 mg/L casein, 30 g/L sucrose, 2 mg/L 6-Benzyladenine, 5 g/L mannose, 8 g/L agar, and pH 5.8) for differentiating culture at 25° C. A plantlet that obtained through differentiation is transferred to the MS rooting medium (2.15 g/L MS salt, MS vitamin, 300 mg/L casein, 30 g/L sucrose, 1 mg/L indole-3-acetic acid, 8 g/L agar, and pH 5.8) and cultured at 25° C. until the plantlet is about 10 cm high, and then the plantlet is transferred to a greenhouse and cultured until it bears fruit. In the greenhouse, the plantlet is cultured for 16 hours at 28° C. and then cultured for 8 hours at 20° C. every day.

2. Verification of PIC9-02 Nucleotide Sequence-Transferred Maize Plant by TagMan About 100 mg leaves of the PIC9-02 nucleotide sequence-transferred maize plant, the PIC9-02 substituted nucleotide sequence-transferred maize plant, the PIC9-02 deleted nucleotide sequence-transferred maize plant, the PIC9-02 added nucleotide sequence-transferred maize plant and the known sequence-transferred maize plant are taken as samples respectively, and their genome DNAs are extracted by using DNeasy Plant Maxi Kit from Qiagen, and the number of the copies of PIC9 gene is detected by Taqman probe fluorescence quantitative PCR method. Meanwhile, under the condition that a wild-type maize plant as negative control, the genome DNAs were detected and analysed based upon the method above. The experiment is repeated 3 times to obtain an average value.

The specific method for detecting the number of the copies of PIC9 gene is as follows:

Step 11, 100 mg leaves of the PIC9-02 nucleotide sequence-transferred maize plant, the PIC9-02 substituted nucleotide sequence-transferred maize plant, the PIC9-02 deleted nucleotide sequence-transferred maize plant, the PIC9-02 added nucleotide sequence-transferred maize plant, the known sequence-transferred maize plant and the wild-type maize plant are taken respectively as samples and grounded into homogenates in a mortar, and 3 replicate are taken for each sample;

Step 12, the genome DNAs of the above samples are extracted using DNeasy Plant Mini Kit from Qiagen, and for the details, please see the product instructions;

Step 13, the genome DNA concentrations of the above samples are measured by using NanoDrop 2000 (Thermo Scientific);

Step 14, the genome DNA concentrations of the above samples are regulated to the same concentration value which is within a range of 80 ng/μl to 100 ng/μl;

Step 15, the number of the copies of these samples is determined by using Taqman probe fluorescence quantitative PCR method, and the samples, whose copy number has been determined, are regarded as standard samples and the sample of the wild-type maize plant is regarded as negative control, and 3 replicate are taken for each sample in order to obtain an average value; the sequences of fluorescence quantitative PCR primers and probes are as follows:

The primers and probes below are used for detecting PIC9-02 nucleotide sequence, PIC9-02 substituted nucleotide sequence, PIC9-02 deleted nucleotide sequence, PIC9-02 added nucleotide sequence:

Primer 1 (CF1): TCATTTGGGGCTTCGTCG shown by SEQ ID NO: 10 in the sequence list;

Primer 2 (CR1): TGATTGATCAGCTGCTCAACCT shown by SEQ ID NO: 11 in the sequence list;

Probe 1 (CP1): CCAGTGGGATGCGTTCCTCGCTC shown by SEQ ID NO: 12 in the sequence list.

The primers and probe below are used for detecting known sequence:

Primer 3 (CF2): CGACTATGCTGTTCGCTGGTAC shown by SEQ ID NO: 13 in the sequence list;

Primer 4 (CR2): GTTGTACCTGACCCAATCACGAG shown by SEQ ID NO: 14 in the sequence list;

Probe 2 (CP2): CGGTCCCCAAACACGTTCGAGTCC shown by SEQ ID NO: 15 in the sequence list.

The PCR reaction system is as follows:

| | |
|---|---|
| JumpStart ™ Taq ReadyMix ™ (Sigma) | 10 μl |
| 50 × primer/probe mixture | 1 μl |
| Genome DNA) | 3 μl |
| Water (ddH$_2$O) | 6 μl |

The 50×primer/probe mixture contains 45 μl each of 1 mM primers, 50 μl 100 μM probe and 860 μl 1×TE buffer solution, and is stored in an amber test tube at 4° C.

The PCR reaction conditions are as follows:

| Step | Temperature | Time |
|---|---|---|
| 21 | 95 C.° | 5 minutes |
| 22 | 95 C.° | 30 seconds |
| 23 | 60 C.° | 1 minute |
| 24 | Return to step 22, repeat 40 times | |

Data is analyzed using SDS2.3 software (Applied Biosystems).

Experiment results shows that, PIC9-02 nucleotide sequence, PIC9-02 substituted nucleotide sequence, PIC9-02 deleted nucleotide sequence, PIC9-02 added nucleotide sequence and known sequence have been all integrated into the genome of the maize plants to be detected, and transgenic maize plants containing single copy of PIC9-02 gene and known sequence are obtained from the PIC9-02 nucleotide sequence-transferred maize plant, the PIC9-02 substituted nucleotide sequence-transferred maize plant, the PIC9-02 deleted nucleotide sequence-transferred maize plant, the PIC9-02 added nucleotide sequence-transferred maize plant and the known sequence-transferred maize plant.

Example 4

Detection for Insecticidal Proteins of Transgenic Maize Plants

1. Detecting the Content of Insecticidal Protein (PIC9 Protein) of Transgenic Maize Plants The solutions involved in this experiment are as follows:

Extraction buffer solution: 8 g/L NaCl, 0.2 g/L $KH_2PO_4$, 2.9 g/L $Na_2HPO_4.12H_2O$, 0.2 g/L KCl, 5.5 ml/L Tween-20, and pH 7.4;

Washing buffer solution: 8 g/L NaCl, 0.2 g/L $KH_2PO_4$, 2.9 g/L $Na_2HPO_4.12H_2O$, 0.2 g/L KCl, 0.5 ml/L Tween-20, and pH 7.4;

Stop solution: 1M HCl.

3 mg fresh leaves of the PIC9-02 nucleotide sequence-transferred maize plant, the PIC9-02 substituted nucleotide sequence-transferred maize plant, the PIC9-02 deleted nucleotide sequence-transferred maize plant, the PIC9-02 added nucleotide sequence-transferred maize plant and the known sequence-transferred maize plant (positive control) are taken as samples respectively. These samples are grounded in liquid nitrogen, then 800 μl the extraction buffer solution are added and centrifuged for 10 minutes at 4000 rpm. Supernatant is diluted by 40-fold using the extraction buffer solution, and 80 μl diluted supernatant is taken for ELISA detection. Since positions 650 to 699 of the PIC9-02 amino acid sequence derives from Cry1Ab, and Domain II (positions 300 to 500) of the PIC9-02 amino acid sequence also has high consistency with Cry1Ab, the antibody of Cry1Ab can be used for detecting the PIC9-02 insecticidal protein. The proportion of the amount of the insecticidal protein (PIC9 protein) in samples based on the fresh weight of leaves is detected and analyzed by ELISA (enzyme-linked immunosorbent assay) kit (Cry1Ab/Cry1Ac kit, from ENVIRLOGIX), and for the details, please see the product instruction.

Meanwhile, the wild-type maize plant and the non-transgenic maize plant identified by fluorescence quantitative PCR are regarded as negative controls, and detected and analyzed according to the above method. There are 20 transformation events (i.e. events) of PIC9-02 nucleotide sequence-transferred plants in total, 10 transformation events (i.e. events) of PIC9-02 substituted nucleotide sequence-transferred plants in total, 10 transformation events (i.e. events) of PIC9-02 deleted nucleotide sequence-transferred plants in total, 10 transformation events (i.e. events) of PIC9-02 added nucleotide sequence-transferred plants in total, 5 transformation events (i.e. events) of known sequence-transferred plants in total, 3 non-transgenic (NGM) plants identified by fluorescence quantitative PCR, and 3 wild-type (CK) plants; this identification is repeated 3 times for each plant.

The experimental results on the content of insecticidal proteins (PIC9-02 proteins) of transgenic maize plants are shown as Table 1. The determined proportions of average expression levels of insecticidal proteins (PIC9-02 proteins) in fresh leaves of the PIC9-02 nucleotide sequence-transferred maize plant, the PIC9-02 substituted nucleotide sequence-transferred maize plant, the PIC9-02 deleted nucleotide sequence-transferred maize plant, the PIC9-02 added nucleotide sequence-transferred maize plant, the known sequence-transferred maize plant, the wild-type maize plant and the non-transgenic maize plant identified by fluorescence quantitative PCR are as follows based on the fresh weight of leaves: 5444.67, 5304.12, 4976.46, 5397.71, 2560.48, −0 and 0, respectively.

TABLE 1

The determined Average Expression Levels of PIC9-02 Proteins in Transgenic Maize Plants

| Plant | PIC9 protein average expression level (ng/g) of single plant (repeated 3 times for each plant) | | | PIC9 protein expression level (ng/g) of each plant Average expression level (ng/g) |
|---|---|---|---|---|
| | 1 | 2 | 3 | |
| PIC9-02 | 5305.26 | 5374.94 | 5653.81 | 5444.67 |
| PIC9-02 substituted | 5136.03 | 5229.49 | 5546.83 | 5304.12 |
| PIC9-02 deleted | 5047.07 | 4951.50 | 4930.82 | 4976.46 |
| PIC9-02 added | 5240.26 | 5502.22 | 5450.65 | 5397.71 |
| Known sequence | 2420.67 | 2720.74 | 2540.04 | 2560.48 |
| NGM | −12.68 | 0 | −11.26 | 0 |
| CK | 0 | −15.13 | −13.21 | 0 |

The above results indicate that, the proportion (ng/g) of average expression level of insecticidal protein in the known sequence-transferred maize plant based on the fresh weight of leaves is 2560.48, and the proportion (ng/g) of average expression level of insecticidal protein in the PIC9-02 nucleotide sequence-transferred maize plant based on the fresh weight of leaves is 5444.67, which is twice as much as the former, and this result indicates that the insecticidal protein in the invention has excellent stability in maize, and the expression level of PIC9-02 protein in maize is raised dramatically by PIC9-02 nucleotide sequence that is optimized according to the preferred codons of maize. Compared with the PIC9-02 nucleotide sequence-transferred maize plant, PIC9-02 protein expression levels of the PIC9-02 substituted nucleotide sequence-transferred maize plant, the PIC9-02 deleted nucleotide sequence-transferred maize plant and the PIC9-02 added nucleotide sequence-transferred maize plant have no significant difference.

2. Detection for the Insecticidal Effects of Transgenic Maize Plants

The insecticidal effects of the PIC9-02 nucleotide sequence-transferred maize plant, the PIC9-02 substituted nucleotide sequence-transferred maize plant, the PIC9-02 deleted nucleotide sequence-transferred maize plant, the PIC9-02 added nucleotide sequence-transferred maize plant, the known sequence-transferred maize plant, the wild-type maize plant and the non-transgenic maize plant identified by fluorescence quantitative PCR against Asian corn borer, cotton bollworm and oriental armyworm are detected respectively.

Figure 4:
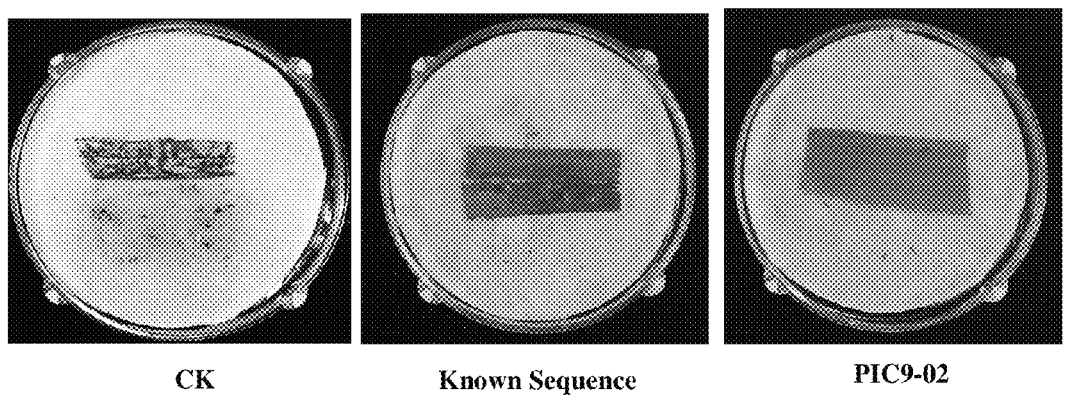
FIG. 4 is an insecticidal effect diagram of transgenic maize plant inoculated with Asian corn borer; CK in FIG. 4 represents wild-type (CK) plants; Known Sequence in FIG. 4 represents known sequence-transferred plants, i.e., SEQ ID NO: 9 transferred plants.
Figure 5:
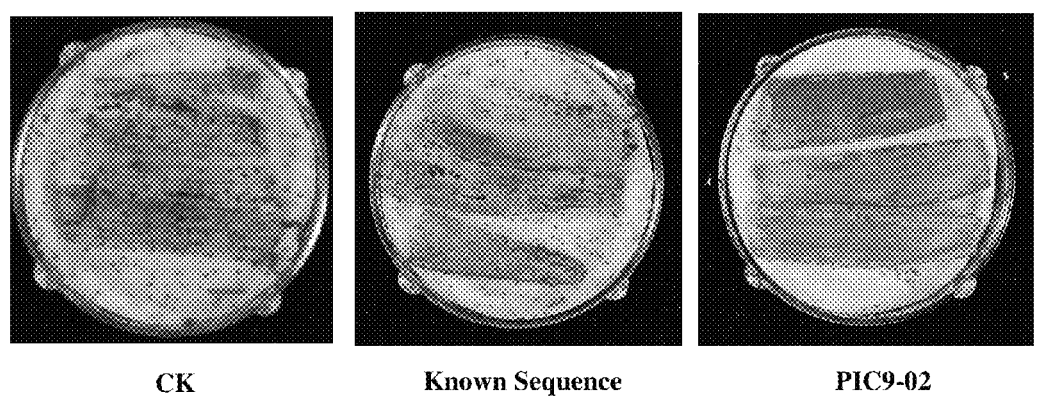
FIG. 5 is an insecticidal effect diagram of transgenic maize plant inoculated with *pseudaletia separata* CK in FIG. 5 represents wild-type (CK) plants; Known Sequence in FIG. 5 represents known sequence-transferred plants, i.e., SEQ ID NO: 9 transferred plants.

(1) Asian corn borer: fresh leaves of the PIC9-02 nucleotide sequence-transferred maize plant, the PIC9-02 substituted nucleotide sequence-transferred maize plant, the PIC9-02 deleted nucleotide sequence-transferred maize plant, the PIC9-02 added nucleotide sequence-transferred maize plant, the known sequence-transferred maize plant, the wild-type maize plant and the non-transgenic maize plant identified by fluorescence quantitative PCR are taken and washed with sterile water, and then water on these leaves is absorbed by gauze. Afterwards, veins of these maize leaves are removed and these leaves are cut into strips of 1 cm×2 cm. One strip of the leaf after cutting is placed on the filter paper at the bottom of a round plastic culture dish, and the filter paper is moistened by distilled water. 10 Asian corn borers which are raised in captivity (newly hatched larvae) are put in each culture dish, and each culture dish for insect test is covered by a lid and then stands for 3 to 5 days at temperature of 26 to 28° C., relative humidity of 70%-80% and photoperiod (light/dark) of 16:8, and then the number of dead larvae is determined to calculate the average mortality of Asian corn borers in each of the samples. There are 20 transformation events (i.e. events) of PIC9-02 nucleotide sequence-transferred plants in total, 10 transformation events (i.e. events) of PIC9-02 substituted nucleotide sequence-transferred plants in total, 10 transformation events (i.e. events) of PIC9-02 deleted nucleotide sequence-transferred plants in total, 10 transformation events (i.e. events) of PIC9-02 added nucleotide sequence-transferred plants in total, 5 transformation events (i.e. events) of known sequence-transferred plants, 3 non-transgenic (NGM) plants identified by fluorescence quantitative PCR, and 3 wild-type (CK) plants; this identification is repeated 3 times for each plant. The results are shown as Table 2 and FIG. 4.

TABLE 2

Experimental Results of Insecticidal Effect of Asian Corn Borer-inoculated Transgenic Maize Plants

| Plant | Asian corn borer mortality (%) of a single plant (repeated 3 times for each plant) | | | Death of Asian corn borer (each plant) |
|---|---|---|---|---|
| | 1 | 2 | 3 | Average mortality (%) |
| PIC9-02 | 100 | 100 | 100 | 100 |
| PIC9-02 substituted | 99 | 95 | 90 | 94.7 |
| PIC9-02 deleted | 95 | 86 | 88 | 89.7 |
| PIC9-02 added | 100 | 96 | 98 | 98 |
| Known sequence | 75 | 79 | 68 | 74 |

TABLE 2-continued

Experimental Results of Insecticidal Effect of Asian Corn Borer-inoculated Transgenic Maize Plants

| Plant | Asian corn borer mortality (%) of a single plant (repeated 3 times for each plant) | | | Death of Asian corn borer (each plant) |
|---|---|---|---|---|
| | 1 | 2 | 3 | Average mortality (%) |
| NGM | 0 | 0 | 0 | 0 |
| CK | 0 | 0 | 0 | 0 |

The results indicate that: plants having certain resistance to Asian corn borer can be selected from the PIC9-02 nucleotide sequence-transferred maize plant and the known sequence-transferred maize plant, however, the test insect mortality of the PIC9-02 nucleotide sequence-transferred maize plant is significantly higher than that of the known sequence-transferred maize plant. The test insect mortality of the PIC9-02 nucleotide sequence-transferred maize plant is above 90%, while the test insect mortality of the known sequence-transferred maize plant is about 70%.

(2) Cotton bollworm: young filaments of the PIC9-02 nucleotide sequence-transferred maize plant, the PIC9-02 substituted nucleotide sequence-transferred maize plant, the PIC9-02 deleted nucleotide sequence-transferred maize plant, the PIC9-02 added nucleotide sequence-transferred maize plant, the known sequence-transferred maize plant, the wild-type maize plant and the non-transgenic maize plant identified by fluorescence quantitative PCR are taken respectively. 20 to 30 filaments are then placed on the filter paper at the bottom of a round plastic culture dish, and the filter paper is moistened by distilled water. 10 cotton bollworms which were raised in captivity (newly hatched larvae) are put in each culture dish, and each culture dish for insect test is covered by a lid and then stands for 3 to 5 days at temperature of 26 to 28° C., relative humidity of 80%-90% and photoperiod (light/dark) of 14:10. The number of dead larvae is counted, and the total score of resistance is calculated according to two indexes including development progress and mortality of larvae: total score=100×mortality+90×(the number of newly hatched larvae/the total number of inoculated larvae)+60×(the number of newly hatched-negative control larvae/the total number of inoculated larvae)+10×(the number of negative control larvae/the total number of inoculated larvae). There are 20 transformation events (i.e. events) of PIC9-02 nucleotide sequence-transferred plants in total, 10 transformation events (i.e. events) of PIC9-02 substituted nucleotide sequence-transferred plants in total, 10 transformation events (i.e. events) of PIC9-02 deleted nucleotide sequence-transferred plants in total, 10 transformation events (i.e. events) of PIC9-02 added nucleotide sequence-transferred plants in total, 5 transformation events (i.e. events) of known sequence-transferred plants, 3 non-transgenic (NGM) plants identified by fluorescence quantitative PCR, and 3 wild-type (CK) plants; this identification is repeated 3 times for each plant. The results are shown as Table 3.

TABLE 3

Experimental Results of Insecticidal Effect of Cotton Bollworm-Inoculated Transgenic Maize Plants

| Plant | Development progress of cotton bollworm (each plant on average) | | | Death of cotton bollworm (each plant on average) | | Total score (each plant) |
|---|---|---|---|---|---|---|
| | New hatching | New hatching-negative control | ≥ negative control | The total number of inoculatd larvae | Mortality (%) | |
| PIC9-02 | 0.5 | 1.8 | 1.7 | 10 | 60 | 77 |
| PIC9-02 substituted | 0 | 3.7 | 2.3 | 10 | 40 | 64.5 |

TABLE 3-continued

Experimental Results of Insecticidal Effect of Cotton Bollworm-Inoculated Transgenic Maize Plants

| Plant | Development progress of cotton bollworm (each plant on average) | | | Death of cotton bollworm (each plant on average) | | Total score (each plant) |
|---|---|---|---|---|---|---|
| | New hatching | New hatching-negative control | ≥ negative control | The total number of inoculatd larvae | Mortality (%) | |
| PIC9-02 deleted | 1 | 2.5 | 3.5 | 10 | 30 | 57.5 |
| PIC9-02 added | 0 | 4 | 1 | 10 | 50 | 75 |
| Known sequence | 0 | 3.8 | 4.7 | 10 | 15 | 42.5 |
| NGM | 0 | 0 | 10 | 10 | 0 | 10 |
| CK | 0 | 0 | 10 | 10 | 0 | 10 |

The results indicate that: plants having certain resistance to cotton bollworm can be selected from the PIC9-02 nucleotide sequence-transferred maize plant and the known sequence-transferred maize plant. However, the bioassay total score of the PIC9-02 nucleotide sequence-transferred maize plant is significantly higher than that of the known sequence-transferred maize plant. The bioassay total score of the PIC9-02 nucleotide sequence-transferred maize plant is above 75, while the bioassay total score of the known sequence-transferred maize plant generally is about 40. The result also indicate that, the PIC9-02 nucleotide sequence-transferred maize plant does not lead to massive death of the newly hatched larvae, but will suppress the development progress of larvae greatly, and specifically, 3 to 5 days later, larvae are still basically in the state of new hatching or between the states of new hatching and negative control.

(3) Oriental armyworm: fresh leaves of the PIC9-02 nucleotide sequence-transferred maize plant, the PIC9-02 substituted nucleotide sequence-transferred maize plant, the PIC9-02 deleted nucleotide sequence-transferred maize plant, the PIC9-02 added nucleotide sequence-transferred maize plant, the known sequence-transferred maize plant, the wild-type maize plant and the non-transgenic maize plant identified by fluorescence quantitative PCR are taken, and thoroughly washed with sterile water and water on these leaves is absorbed by gauze. Afterwards, veins of these maize leaves are removed and these leaves are cut into strips of 1 cm×2 cm. 3 strip-shaped leaves after cutting are placed on the filter paper at the bottom of a round plastic culture dish, and the filter paper is moistened by distilled water. 10 oriental armyworms which are raised in captivity (newly hatched larvae) are put in each culture dish, and each culture dish for insect test is covered by a lid and then stands for 3 to 5 days at temperature of 26 to 28° C., relative humidity of 80%-90% and photoperiod (light/dark) of 14:10. The total score of resistance is obtained according to three indexes including development progress of oriental armyworm larvae, mortality and damage ratio of leaves: total score=100×mortality+90×(the number of newly hatched larvae/the total number of inoculated larvae)+60×(the number of newly hatched-negative control larvae/the total number of inoculated larvae)+10×(the number of negative control larvae/the total number of inoculated larvae)+100×(1-damage ratio of leaves). There are 20 transformation events (i.e. events) of PIC9-02 nucleotide sequence-transferred plants in total, 10 transformation events (i.e. events) of PIC9-02 substituted nucleotide sequence-transferred plants in total, 10 transformation events (i.e. events) of PIC9-02 deleted nucleotide sequence-transferred plants in total, 10 transformation events (i.e. events) of PIC9-02 added nucleotide sequence-transferred plants in total, 5 transformation events (i.e. events) of known sequence-transferred plants, 3 non-transgenic (NGM) plants identified by fluorescence quantitative PCR, and 3 wild-type (CK) plants; this identification is repeated 3 times for each plant. The results are shown as Table 4 and Table 5.

The results indicate that: plants having certain resistance to oriental armyworm can be selected from the PIC9-02 nucleotide sequence-transferred maize plant and the known sequence-transferred maize plant. However, the bioassay total score of the PIC9 nucleotide sequence-transferred maize plant is significantly higher than that of the known sequence-transferred maize plant. The bioassay total score of the PIC9-02 nucleotide sequence-transferred maize plant is above 150, while the bioassay total score of the known sequence-transferred maize plant is about 90. The result also indicates that, the PIC9-02 nucleotide sequence-transferred maize plant does not lead to massive death of the newly hatched larvae, but will suppress the development progress of larvae greatly, that is to say, and more specially, 3 to 5 days later, larvae are still basically in the state of new hatching or between the states of new hatching and negative control, and the damage ratio of leaves is below 30%.

It is proved that the optimized PIC9-02 nucleotide sequence-transferred maize plant has high insect resistance. That is to say, the PIC9-02 nucleotide sequence-transferred maize plant, having high PIC9-02 protein expression level, have high toxicity, so that the expression toxicity of PIC9-02 protein in maize is remarkably raised by PIC9-02 nucleotide sequence optimized according to the preferred codons of maize. In addition, compared with the PIC9-02 nucleotide sequence-transferred maize plant, PIC9-02 protein toxicities of the PIC9-02 substituted nucleotide sequence-transferred maize plant, the PIC9-02 deleted nucleotide sequence-transferred maize plant and the PIC9-02 added nucleotide sequence-transferred maize plant have no significant difference.

TABLE 4

Experimental Results of Insecticidal Effect of Oriental Armyworm-Inoculated Transgenic Maize Plants

| Plant | Damage rate (%) of leaves | Development progress of oriental armyworm (each plant on average) | | | Death of oriental armyworm (each plant on average) | | Total score (each plant) |
| --- | --- | --- | --- | --- | --- | --- | --- |
| | | New hatching | New hatching-negative control | ≥ negative control | Total number of inoculated larvae | Mortality (%) | |
| PIC9-02 | 10 | 1 | 5 | 0 | 10 | 40 | 169 |
| PIC9-02 substituted | 20 | 1 | 4 | 3 | 10 | 20 | 136 |
| PIC9-02 deleted | 30 | 0 | 6 | 3 | 10 | 10 | 119 |
| PIC9-02 added | 15 | 1 | 5 | 1 | 10 | 30 | 155 |
| Known sequence | 40 | 0 | 3.9 | 6.1 | 10 | 0 | 89.5 |
| NGM | 95 | 0 | 0 | 10 | 10 | 0 | 15 |
| CK | 98 | 0 | 0 | 10 | 10 | 0 | 12 |

In brief, the insecticidal gene of the invention, which adopts preferred codons of maize, is completely in conformity with the features of maize gene, so that the insecticidal gene of the invention is particularly suitable for expression in monocotyledons, especially in maize. The PIC9-02 protein of the invention not only has high expression level and good stability, but also has strong toxicity against insect pests, especially against Lepidoptera insect pests.

It should be finally pointed out that the above examples are just used to illustrate the technical solutions of the invention but not to limit the invention; while the invention has been described in details with reference to the preferred examples, it shall be understood by an ordinary person skilled in the art that modifications or equivalent substitutions can be made to the technical solutions of the invention without departing from the spirit and scope of the invention.

What claimed is:

1. An insecticidal protein, comprising:
   (a) a protein consisting of the amino acid sequence of SEQ ID NO:2; or
   (b) a protein encoded by the nucleic acid sequence of SEQ ID NO:3; or
   (c) a protein encoded by the nucleic acid sequence of SEQ ID NO:4; or
   (d) a protein encoded by the nucleic acid sequence of SEQ ID NO:5.

2. A method for controlling insect pests, comprising contacting the insect pests with an inhibitory amount of the insecticidal protein of claim 1, wherein the insect pests are Lepidoptera insect pests.

3. The method for controlling insect pests according to claim 2, wherein the insecticidal protein is produced from a transgenic host organism, and wherein the transgenic host organism is selected from the group consisting of plant cells, animal cells, bacteria, yeast, baculovirus, nematodes and algae.

4. The method for controlling insect pests according to claim 3, wherein the plant is maize, soybean, cotton, rice or wheat.

5. The method for controlling insect pests according to claim 4, wherein the insecticidal protein is expressed in the plant together with at least one second insecticidal protein that is different from the insecticidal protein of SEQ ID NO:2 and the insecticidal proteins encoded by SEQ NOs: 3, 4, and 5.

6. The method for controlling insect pests according to claim 5, wherein the second insecticidal protein is a Vip-type insecticidal protein, a protease inhibitor, an agglutinin, an α-amylase or a peroxidase.

* * * * *

```
                        SEQUENCE LISTING

<160> NUMBER OF SEQ ID NOS: 15

<210> SEQ ID NO 1
<211> LENGTH: 2100
<212> TYPE: DNA
<213> ORGANISM: Artificial Sequence
<220> FEATURE:
<223> OTHER INFORMATION: PIC9-02 Nucleotide Sequence

<400> SEQUENCE: 1
atgaagaata gcatcaagct gtcggagctg tggtacttca acgagcgcaa gtggaggtac      60
ttcatggaga tcgtcaacaa tcagaatcag tgcgtcccat acaactgcct caacaatcct     120
gagatcgaga ttctggaggg cgggaggatc tccgtgggca acactccgat cgacatttct     180
ctctcactga cccagttcct cctgagcgag ttcgtgccag gcgctgggtt cgtcctcggc     240
ctgatcgacc tcatttgggg cttcgtcggg ccatcccagt gggatgcgtt cctcgctcag     300
gttgagcagc tgatcaatca gcgcatcgcc gaggctgtga ggaacaccgc catccaggag     360
ctggagggca tggctagggt ctaccggacc tacgctacgg ctttcgctga gtgggagaag     420
gccccggacg atccagagct cagggaggct ctgaggaccc agttcactgc caccgagacg     480
tacatctccg gcaggattag cgtgctcaag atccagacgt tcgaggtcca gctcctgtct     540
gttttcgcgc aggccgcgaa cctccacctg tcactcctgc gcgacgtggt cttcttcggc     600
cagcgctggg ggttcagcac cacgacagtc aacaattact acaacgacct cactgagggc     660
atctcgacat acactgatta cgccgtgcgg tggtacaaca ccgggctgga gagggtttgg     720
ggcccagaca gcagggattg ggtgcggtac aatcagttcc gcagggagct caccctgacg     780
gtgctcgaca tcgtcgcgct gttcccgaac tacgattcac ggcgctaccc catcaggacc     840
gtctcccagc tcacgcggga gatctacaca aatcagttc tggagaactt cgacggctcg     900
```

```
ttccgcgggt ctgctcaggg catcgagagg tcaattaggt cccctcatct catggacatc    960
ctgaactcga tcacaatcta cactgatgcg cacaggggt actactactg gtctggccat   1020
cagatcatgg cttcaccagt gggcttctcc gggccagagt tcactttccc cctgtacggc   1080
accatgggca acgccgcccc gcagcagcgc atcgttgctc agctcggcca ggggtgtac   1140
aggacactgt ccagcacttt ctacaggcgg ccgttcaaca tcggcattaa caatcagcag   1200
ctctccgtcc tggacgggac ggagttcgct tacggcacat cgtctaacct cccaagcgct   1260
gtctaccgca agagcggcac ggttgactcg ctggatgaga tcccgcccca gaacaataac   1320
gtgccacctc ggcagggctt ctcccacagg ctcagccatg tttcgatgtt caggtccggc   1380
tcatccagct cggtgagcat cattagggcc cccatgttct cttggatcca ccggtcagcg   1440
gagttcaata acatcatcgc ctccgacagc atcacccaga ttccagcggt caaggggaat   1500
ttcctgttca acggctctgt tatctcaggc cctgggttca ccggcgggga tctcgtccgg   1560
ctgaattctt cagggaataa cattcagaac cgcggctaca tcgaggtgcc aattcacttc   1620
ccttcgacat ctactcgcta caggttcggg gtgcgctacg ctagcgtgac gccaatccac   1680
ctcaacgtga actgggggcaa ttccagcatt ttcagcaaca cagtgcctgc caccgcgacg   1740
tcgctcgaca atctgcagtc gtctgatttc ggctacttcg agtccgctaa cgccttcacg   1800
tcatccctgg ggaatatcgt cggcgttagg aacttcagcg gcacagcggg cgtgatcatc   1860
gaccggttcg agttcatccc ggtcacagcc actctcgagg cggagtacaa cctggagagg   1920
gctcagaagg ctgtgaacgc cctcttcacc tcctcgaacc agatcggcct gaagaccgac   1980
gtgacggatt accacatcga ccaggtttcg aacctcgtgg agtgcctgtc tgatgagttc   2040
tgcctggatg agaagaagga gctgtctgag aaggtgaagc acgccaagcg gctgtcgtag   2100
```

<210> SEQ ID NO 2
<211> LENGTH: 699
<212> TYPE: PRT
<213> ORGANISM: Artificial Sequence
<220> FEATURE:
<223> OTHER INFORMATION: PIC9-02 Amino Acid Sequence

<400> SEQUENCE: 2

Met Lys Asn Ser Ile Lys Leu Ser Glu Leu Trp Tyr Phe Asn Glu Arg
1               5                   10                  15

Lys Trp Arg Tyr Phe Met Glu Ile Val Asn Asn Gln Asn Gln Cys Val
            20                  25                  30

Pro Tyr Asn Cys Leu Asn Asn Pro Glu Ile Glu Ile Leu Glu Gly Gly
        35                  40                  45

Arg Ile Ser Val Gly Asn Thr Pro Ile Asp Ile Ser Leu Ser Leu Thr
    50                  55                  60

Gln Phe Leu Leu Ser Glu Phe Val Pro Gly Ala Gly Phe Val Leu Gly
65                  70                  75                  80

Leu Ile Asp Leu Ile Trp Gly Phe Val Gly Pro Ser Gln Trp Asp Ala
                85                  90                  95

Phe Leu Ala Gln Val Glu Gln Leu Ile Asn Gln Arg Ile Ala Glu Ala
            100                 105                 110

Val Arg Asn Thr Ala Ile Gln Glu Leu Glu Gly Met Ala Arg Val Tyr
        115                 120                 125

Arg Thr Tyr Ala Thr Ala Phe Ala Glu Trp Glu Lys Ala Pro Asp Asp
    130                 135                 140

Pro Glu Leu Arg Glu Ala Leu Arg Thr Gln Phe Thr Ala Thr Glu Thr
145                 150                 155                 160

```
Tyr Ile Ser Gly Arg Ile Ser Val Leu Lys Ile Gln Thr Phe Glu Val
            165                 170                 175

Gln Leu Leu Ser Val Phe Ala Gln Ala Ala Asn Leu His Leu Ser Leu
        180                 185                 190

Leu Arg Asp Val Val Phe Phe Gly Gln Arg Trp Gly Phe Ser Thr Thr
        195                 200                 205

Thr Val Asn Asn Tyr Tyr Asn Asp Leu Thr Glu Gly Ile Ser Thr Tyr
    210                 215                 220

Thr Asp Tyr Ala Val Arg Trp Tyr Asn Thr Gly Leu Glu Arg Val Trp
225                 230                 235                 240

Gly Pro Asp Ser Arg Asp Trp Val Arg Tyr Asn Gln Phe Arg Arg Glu
                245                 250                 255

Leu Thr Leu Thr Val Leu Asp Ile Val Ala Leu Phe Pro Asn Tyr Asp
                    260                 265                 270

Ser Arg Arg Tyr Pro Ile Arg Thr Val Ser Gln Leu Thr Arg Glu Ile
            275                 280                 285

Tyr Thr Asn Pro Val Leu Glu Asn Phe Asp Gly Ser Phe Arg Gly Ser
    290                 295                 300

Ala Gln Gly Ile Glu Arg Ser Ile Arg Ser Pro His Leu Met Asp Ile
305                 310                 315                 320

Leu Asn Ser Ile Thr Ile Tyr Thr Asp Ala His Arg Gly Tyr Tyr Tyr
                325                 330                 335

Trp Ser Gly His Gln Ile Met Ala Ser Pro Val Gly Phe Ser Gly Pro
                340                 345                 350

Glu Phe Thr Phe Pro Leu Tyr Gly Thr Met Gly Asn Ala Ala Pro Gln
            355                 360                 365

Gln Arg Ile Val Ala Gln Leu Gly Gln Gly Val Tyr Arg Thr Leu Ser
    370                 375                 380

Ser Thr Phe Tyr Arg Arg Pro Phe Asn Ile Gly Ile Asn Asn Gln Gln
385                 390                 395                 400

Leu Ser Val Leu Asp Gly Thr Glu Phe Ala Tyr Gly Thr Ser Ser Asn
                405                 410                 415

Leu Pro Ser Ala Val Tyr Arg Lys Ser Gly Thr Val Asp Ser Leu Asp
                420                 425                 430

Glu Ile Pro Pro Gln Asn Asn Asn Val Pro Pro Arg Gln Gly Phe Ser
            435                 440                 445

His Arg Leu Ser His Val Ser Met Phe Arg Ser Gly Ser Ser Ser Ser
    450                 455                 460

Val Ser Ile Ile Arg Ala Pro Met Phe Ser Trp Ile His Arg Ser Ala
465                 470                 475                 480

Glu Phe Asn Asn Ile Ile Ala Ser Asp Ser Ile Thr Gln Ile Pro Ala
                485                 490                 495

Val Lys Gly Asn Phe Leu Phe Asn Gly Ser Val Ile Ser Gly Pro Gly
            500                 505                 510

Phe Thr Gly Gly Asp Leu Val Arg Leu Asn Ser Ser Gly Asn Asn Ile
    515                 520                 525

Gln Asn Arg Gly Tyr Ile Glu Val Pro Ile His Phe Pro Ser Thr Ser
530                 535                 540

Thr Arg Tyr Arg Val Arg Val Arg Tyr Ala Ser Val Thr Pro Ile His
545                 550                 555                 560

Leu Asn Val Asn Trp Gly Asn Ser Ser Ile Phe Ser Asn Thr Val Pro
                565                 570                 575
```

```
Ala Thr Ala Thr Ser Leu Asp Asn Leu Gln Ser Ser Asp Phe Gly Tyr
            580                 585                 590

Phe Glu Ser Ala Asn Ala Phe Thr Ser Ser Leu Gly Asn Ile Val Gly
        595                 600                 605

Val Arg Asn Phe Ser Gly Thr Ala Gly Val Ile Ile Asp Arg Phe Glu
    610                 615                 620

Phe Ile Pro Val Thr Ala Thr Leu Glu Ala Glu Tyr Asn Leu Glu Arg
625                 630                 635                 640

Ala Gln Lys Ala Val Asn Ala Leu Phe Thr Ser Ser Asn Gln Ile Gly
            645                 650                 655

Leu Lys Thr Asp Val Thr Asp Tyr His Ile Asp Gln Val Ser Asn Leu
            660                 665                 670

Val Glu Cys Leu Ser Asp Glu Phe Cys Leu Asp Glu Lys Lys Glu Leu
        675                 680                 685

Ser Glu Lys Val Lys His Ala Lys Arg Leu Ser
            690                 695

<210> SEQ ID NO 3
<211> LENGTH: 2100
<212> TYPE: DNA
<213> ORGANISM: Artificial Sequence
<220> FEATURE:
<223> OTHER INFORMATION: PIC9-02 Substituted Nucleotide Sequence

<400> SEQUENCE: 3
```

| | | | | | |
|---|---|---|---|---|---|
| atgaagaata | gcatcaagct | gtcggagctg | tggtacttca | acgagcgcaa | gtggaggtac | 60 |
| ttcatggaga | tcgtcaacaa | tcagaatcag | tgcgtcccat | acaactgcct | caacaatcct | 120 |
| gagatcgaga | ttctggaggg | cgggaggatc | tccgtgggca | cactccgatc | gacatttct | 180 |
| ctctcactga | cccagttcct | cctgagcgag | ttcgtgccag | cgctgggtt | cgtcctcggc | 240 |
| ctgatcgacc | tcatttgggg | cttcgtcggg | ccatcccagt | gggatgcgtt | cctcgctcag | 300 |
| gttgagcagc | tgatcaatca | gcgcatcgcc | gaggctgtga | ggaacaccgc | catccaggag | 360 |
| ctggagggca | tggctagggt | ctaccggacc | tacgctacgg | ctttcgctga | gtgggagaag | 420 |
| gccccggacg | atccagagct | cagggaggct | ctgaggaccc | agttcactgc | caccgagacg | 480 |
| tacatctccg | gcaggattag | cgtgctcaag | atccagacgt | tcgaggtcca | gctcctgtct | 540 |
| gttttcgcgc | aggccgcgaa | cctccacctg | tcactcctgc | gcgacgtggt | cttcttcggc | 600 |
| cagcgctggg | ggttcagcac | cacgacagtc | aacaattact | acaacgacct | cactgagggc | 660 |
| atctcgacat | acactgatta | cgccgtgcgg | tggtacaaca | ccgggctgga | gagggtttgg | 720 |
| ggcccagaca | gcagggattg | ggtgcggtac | aatcagttcc | gcagggagct | caccctgacg | 780 |
| gtgctcgaca | tcgtcgcgct | gttccccgaac | tacgattcac | ggcgctaccc | catcaggacc | 840 |
| gtctcccagc | tcacgcggga | gatctacaca | aatccagttc | tggagaactt | cgacggctcg | 900 |
| ttccgcgggt | ctgctcaggg | catcgagagg | tcaattaggt | cccctcatct | catggacatc | 960 |
| ctgaactcga | tcacaatcta | cactgatgcg | cacagggggt | actactactg | gtctggccat | 1020 |
| cagatcatgg | cttcaccagt | gggcttctcc | gggccagagt | tcactttccc | cctgtacggc | 1080 |
| accatgggca | acgccgcccc | gcagcagcgc | atcgttgctc | agctcggcca | ggggtgtac | 1140 |
| aggacactgt | ccagcacttt | ctacaggcgg | ccgttcaaca | tcggcattaa | caatcagcag | 1200 |
| ctctccgtcc | tggacgggac | ggagttcgct | tacggcacat | cgtctaacct | cccaagcgct | 1260 |
| gtctaccgca | agagcggcac | ggttgactcg | ctggatgaga | tccgccccca | gaacaataac | 1320 |
| gtgccaccctc | ggcagggctt | ctcccacagg | ctcagccatg | tttcgatgtt | caggtccggc | 1380 |

-continued

| | |
|---|---|
| tcatccagct cggtgagcat cattagggcc cccatgttct cttggatcca ccggtcagcg | 1440 |
| gagttcaata acatcatcgc ctccgacagc atcacccaga ttccagcggt caagggggaat | 1500 |
| ttcctgttca acggctctgt tatctcaggc cctgggttca ccggcgggga tctcgtccgg | 1560 |
| ctgaattctt cagggaataa cattcagaac cgcggctaca tcgaggtgcc aattcacttc | 1620 |
| ccttcgacat ctactcgcta cagggttcgg gtgcgctacg ctagcgtgac gccaatccac | 1680 |
| ctcaacgtga actggggcaa ttccagcatt ttcagcaaca cagtgcctgc caccgcgacg | 1740 |
| tcgctcgaca atctgcagtc gtctgatttc ggctacttcg agtccgctaa cgccttcacg | 1800 |
| tcatccctgg ggaatatcgt cggcgttagg aacttcagcg gcacagcggg cgtgatcatc | 1860 |
| gaccggttcg agttcatccc ggtcacagcc actctcgagg cggagtacaa cctggagagg | 1920 |
| gctcagaagg ctgtgaacgc cctcttcacc tcctcgaacc agatcggcct gaagaccgac | 1980 |
| gtgacggatt accacatcga ccaggtttcg aacctcgtgg agtacctgtc tgatgagttc | 2040 |
| tgcctggatg agaagaagga gctgtctgag aaggtgaagc acgccaagcg gctgtcgtag | 2100 |

<210> SEQ ID NO 4
<211> LENGTH: 2070
<212> TYPE: DNA
<213> ORGANISM: Artificial Sequence
<220> FEATURE:
<223> OTHER INFORMATION: PIC9-02 Deleted Nucleotide Sequence

<400> SEQUENCE: 4

| | |
|---|---|
| atgaagaata gcatcaagct gtcggagctg tggtacttca cgagcgcaa gtggaggtac | 60 |
| ttcatggaga tcgtcaacaa tcagaatcag tgcgtcccat acaactgcct caacaatcct | 120 |
| gagatcgaga ttctggaggg cgggaggatc tccgtgggca acactccgat cgacatttct | 180 |
| ctctcactga cccagttcct cctgagcgag ttcgtgccag cgctgggtt cgtcctcggc | 240 |
| ctgatcgacc tcatttgggg cttcgtcggg ccatcccagt gggatgcgtt cctcgctcag | 300 |
| gttgagcagc tgatcaatca gcgcatcgcc gaggctgtga ggaacaccgc catccaggag | 360 |
| ctggagggca tggctagggt ctaccggacc tacgctacgg cttttcgctga gtgggagaag | 420 |
| gccccggacg atccagagct cagggaggct ctgaggaccc agttcactgc caccgagacg | 480 |
| tacatctccg gcaggattag cgtgctcaag atccagacgt tcgaggtcca gctcctgtct | 540 |
| gttttcgcgc aggccgcgaa cctccacctg tcactcctgc gcgacgtggt cttcttcggc | 600 |
| cagcgctggg ggttcagcac cacgacagtc aacaattact acaacgacct cactgagggc | 660 |
| atctcgacat acactgatta cgccgtgcgg tggtacaaca ccgggctgga gagggtttgg | 720 |
| ggcccagaca gcagggattg ggtgcggtac aatcagttcc gcagggagct caccctgacg | 780 |
| gtgctcgaca tcgtcgcgct gttccccgaac tacgattcac ggcgctaccc catcaggacc | 840 |
| gtctcccagc tcacgcggga gatctacaca aatccagttc tggagaactt cgacggctcg | 900 |
| ttccgcgggt ctgctcaggg catcgagagg tcaattaggt cccctcatct catggacatc | 960 |
| ctgaactcga tcacaatcta cactgatgcg cacagggggt actactactg gtctggccat | 1020 |
| cagatcatgg cttccagt gggcttctcc gggccagagt tcactttccc cctgtacggc | 1080 |
| accatgggca acgccgcccc gcagcagcgc atcgttgctc agctcggcca gggggtgtac | 1140 |
| aggacactgt ccagcacttt ctacaggcgg ccgttcaaca tcggcattaa caatcagcag | 1200 |
| ctctccgtcc tggacgggac ggagttcgct tacggcacat cgtctaacct cccaagcgct | 1260 |
| gtctaccgca gagcggcac ggttgactcg ctggatgaga tccgccccca gaacaataac | 1320 |
| gtgccacctc ggcagggctt ctcccacagg ctcagccatg tttcgatgtt caggtccggc | 1380 |

|  |  |
|---|---|
| tcatccagct cggtgagcat cattagggcc cccatgttct cttggatcca ccggtcagcg | 1440 |
| gagttcaata acatcatcgc ctccgacagc atcacccaga ttccagcggt caagggaat | 1500 |
| ttcctgttca acggctctgt tatctcaggc cctgggttca ccggcgggga tctcgtccgg | 1560 |
| ctgaattctt cagggaataa cattcagaac cgcggctaca tcgaggtgcc aattcacttc | 1620 |
| ccttcgacat ctactcgcta cagggttcgg gtgcgctacg ctagcgtgac gccaatccac | 1680 |
| ctcaacgtga actggggcaa ttccagcatt ttcagcaaca cagtgcctgc caccgcgacg | 1740 |
| tcgctcgaca atctgcagtc gtctgatttc ggctacttcg agtccgctaa cgccttcacg | 1800 |
| tcatccctgg ggaatatcgt cggcgttagg aacttcagcg gcacagcggg cgtgatcatc | 1860 |
| gaccggttcg agttcatccc ggtcacagcc actctcgagg cggagtacaa cctggagagg | 1920 |
| tcctcgaacc agatcggcct gaagaccgac gtgacggatt accacatcga ccaggtttcg | 1980 |
| aacctcgtgg agtgcctgtc tgatgagttc tgcctggatg agaagaagga gctgtctgag | 2040 |
| aaggtgaagc acgccaagcg gctgtcgtag | 2070 |

<210> SEQ ID NO 5
<211> LENGTH: 2115
<212> TYPE: DNA
<213> ORGANISM: Artificial Sequence
<220> FEATURE:
<223> OTHER INFORMATION: PIC9-02 Added Nucleotide Sequence

<400> SEQUENCE: 5

|  |  |
|---|---|
| atgaagaata gcatcaagct gtcggagctg tggtacttca cgagcgcaa gtggaggtac | 60 |
| ttcatggaga tcgtcaacaa tcagaatcag tgcgtcccat acaactgcct caacaatcct | 120 |
| gagatcgaga ttctggaggg cgggaggatc tccgtgggca cactccgat cgacatttct | 180 |
| ctctcactga cccagttcct cctgagcgag ttcgtgccag cgctgggtt cgtcctcggc | 240 |
| ctgatcgacc tcatttgggg cttcgtcggg ccatcccagt gggatgcgtt cctcgctcag | 300 |
| gttgagcagc tgatcaatca gcgcatcgcc gaggctgtga ggaacaccgc catccaggag | 360 |
| ctggagggca tggctagggt ctaccggacc tacgctacgg cttcgctga gtgggagaag | 420 |
| gccccggacg atccagagct caggggaggct ctgaggaccc agttcactgc caccgagacg | 480 |
| tacatctccg gcaggattag cgtgctcaag atccagacgt tcgaggtcca gctcctgtct | 540 |
| gttttcgcgc aggccgcgaa cctccacctg tcactcctgc gcgacgtggt cttcttcggc | 600 |
| cagcgctggg ggttcagcac cacgacagtc aacaattact acaacgacct cactgagggc | 660 |
| atctcgacat acactgatta cgccgtgcgg tggtacaaca ccgggctgga gagggtttgg | 720 |
| ggcccagaca gcagggattg ggtgcggtac aatcagttcc gcagggagct caccctgacg | 780 |
| gtgctcgaca tcgtcgcgct gttcccgaac tacgattcac ggcgctaccc catcaggacc | 840 |
| gtctcccagc tcacgcggga gatctacaca atccagttc tggagaactt cgacggctcg | 900 |
| ttccgcgggt ctgctcaggg catcgagagg tcaattaggt cccctcatct catggacatc | 960 |
| ctgaactcga tcacaatcta cactgatgcg cacagggggt actactactg gtctggccat | 1020 |
| cagatcatgg cttcaccagt gggcttctcc gggccagagt tcactttccc cctgtacggc | 1080 |
| accatgggca acgccgcccc gcagcagcgc atcgttgctc agctcggcca gggggtgtac | 1140 |
| aggacactgt ccagcacttt ctacaggcgg ccgttcaaca tcggcattaa caatcagcag | 1200 |
| ctctccgtcc tggacgggac ggagttcgct tacggcacat cgtctaacct cccaagcgct | 1260 |
| gtctaccgca gagcggcac ggttgactcg ctggatgaga tccgccccca gaacaataac | 1320 |
| gtgccacctc ggcagggctt ctcccacagg ctcagccatg tttcgatgtt caggtccggc | 1380 |

-continued

```
tcatccagct cggtgagcat cattagggcc cccatgttct cttggatcca ccggtcagcg    1440
gagttcaata acatcatcgc ctccgacagc atcacccaga ttccagcggt caagggggaat    1500 ttcctgttca acggctctgt tatctcaggc cctgggttca ccggcgggga tctcgtccgg    1560
ctgaattctt cagggaataa cattcagaac cgcggctaca tcgaggtgcc aattcacttc    1620
ccttcgacat ctactcgcta cagggttcgg gtgcgctacg ctagcgtgac gccaatccac    1680
ctcaacgtga actggggcaa ttccagcatt ttcagcaaca cagtgcctgc caccgcgacg    1740
tcgctcgaca atctgcagtc gtctgatttc ggctacttcg agtccgctaa cgccttcacg    1800
tcatccctgg ggaatatcgt cggcgttagg aacttcagcg gcacagcggg cgtgatcatc    1860
gaccggttcg agttcatccc ggtcacagcc actctcgagg cggagtacaa cctggagagg    1920
gctcagaagg ctgtgaacgc cctcttcacc tcctcgaacc agatcggcct gaagaccgac    1980
gtgacggatt accacatcga ccaggtttcg aacctcgtgg agtgcctgtc tgatgagttc    2040
tgcctggatg agaagaagga gctgtctgag aaggtgaagc acgccaagcg gctgtcggat    2100
gaacgcaatt tatag                                                    2115
```

<210> SEQ ID NO 6
<211> LENGTH: 1992
<212> TYPE: DNA
<213> ORGANISM: Zea mays

<400> SEQUENCE: 6

```
ctgcagtgca gcgtgacccg gtcgtgcccc tctctagaga taatgagcat tgcatgtcta      60
agttataaaa aattaccaca tattttttt gtcacacttg tttgaagtgc agtttatcta     120
tctttataca tatatttaaa ctttactcta cgaataatat aatctatagt actacaataa     180
tatcagtgtt ttagagaatc atataaatga acagttagac atggtctaaa ggacaattga     240
gtattttgac aacaggactc tacagtttta tcttttttagt gtgcatgtgt tctccttttt     300
ttttgcaaat agcttcacct atataatact tcatccattt tattagtaca tccatttagg     360
gtttagggtt aatggttttt atagactaat tttttttagta catctatttt attctatttt     420
agcctctaaa ttaagaaaac taaaactcta ttttagtttt tttatttaat aattttagata     480 taaaatagaa taaaataaag tgactaaaaa ttaaacaaat acccctttaag aaattaaaaa     540 aactaaggaa acattttctt tgtttcgagt agataatgcc agcctgttaa acgccgtcga     600
cgagtctaac ggacaccaac cagcgaacca gcagcgtcgc gtcgggccaa gcgaagcaga     660
cggcacggca tctctgtcgc tgcctctgga cccctctcga gagttccgct ccaccgttgg     720
acttgctccg ctgtcggcat ccagaaattg cgtggcggag cggcagacgt gagccggcac     780
ggcaggcggc ctcctcctcc tctcacggca cggcagctac gggggattcc tttcccaccg     840
ctccttcgct ttcccttcct cgcccgccgt aataaataga caccccctcc acaccctctt     900
tccccaacct cgtgttgttc ggagcgcaca cacacacaac cagatctccc ccaaatccac     960
ccgtcggcac ctccgcttca aggtacgccg ctcgtcctcc cccccccccc ctctctacct    1020
tctctagatc ggcgttccgg tccatggtta gggcccggta gttctacttc tgttcatgtt    1080
tgtgttagat ccgtgtttgt gttagatccg tgctgctagc gttcgtacac ggatgcgacc    1140
tgtacgtcag acacgttctg attgctaact tgccagtgtt tctctttggg gaatcctggg    1200
atggctctag ccgttccgca gacgggatcg atttcatgat ttttttttgtt tcgttgcata    1260 gggtttggtt tgccctttc ctttatttca atatatgccg tgcacttgtt tgtcgggtca    1320
tcttttcatg ctttttttg tcttggttgt gatgatgtgg tctggttggg cggtcgttct    1380
```

```
agatcggagt agaattctgt tcaaaactac ctggtggatt tattaatttt ggatctgtat    1440
gtgtgtgcca tacatattca tagttacgaa ttgaagatga tggatggaaa tatcgatcta    1500
ggataggtat acatgttgat gcgggtttta ctgatgcata tacagagatg cttttttgttc   1560 gcttggttgt gatgatgtgg tgtggttggg cggtcgttca ttcgttctag atcggagtag    1620
aatactgttt caaactacct ggtgtattta ttaattttgg aactgtatgt gtgtgtcata    1680
catcttcata gttacgagtt taagatggat ggaaatatcg atctaggata ggtatacatg    1740
ttgatgtggg ttttactgat gcatatacat gatggcatat gcagcatcta ttcatatgct    1800
ctaaccttga gtacctatct attataataa acaagtatgt tttataatta ttttgatctt    1860
gatatacttg gatgatggca tatgcagcag ctatatgtgg atttttttag ccctgccttc    1920
atacgctatt tatttgcttg gtactgtttc ttttgtcgat gctcaccctg ttgtttggtg    1980
ttacttctgc ag                                                        1992

<210> SEQ ID NO 7
<211> LENGTH: 253
<212> TYPE: DNA
<213> ORGANISM: Agrobacterium tumefaciens

<400> SEQUENCE: 7
gatcgttcaa acatttggca ataaagtttc ttaagattga atcctgttgc cggtcttgcg     60
atgattatca tataatttct gttgaattac gttaagcatg taataattaa catgtaatgc    120
atgacgttat ttatgagatg ggttttatg attagagtcc cgcaattata catttaatac     180
gcgatagaaa acaaaatata gcgcgcaaac taggataaat tatcgcgcgc ggtgtcatct    240
atgttactag atc                                                       253

<210> SEQ ID NO 8
<211> LENGTH: 1176
<212> TYPE: DNA
<213> ORGANISM: Escherichia coli

<400> SEQUENCE: 8
atgcaaaaac tcattaactc agtgcaaaac tatgcctggg gcagcaaaac ggcgttgact     60
gaactttatg gtatggaaaa tccgtccagc cagccgatgg ccgagctgtg gatgggcgca    120
catccgaaaa gcagttcacg agtgcagaat gccgccggag atatcgtttc actgcgtgat    180
gtgattgaga gtgataaatc gactctgctc ggagaggccg ttgccaaacg ctttggcgaa    240 ctgccttttcc tgttcaaagt attatgcgca gcacagccac tctccattca ggttcatcca    300
aacaaacaca attctgaaat cggttttgcc aaagaaaatg ccgcaggtat cccgatggat    360
gccgccgagc gtaactataa agatcctaac cacaagccgg agctggtttt tgcgctgacg    420
cctttccttg cgatgaacgc gtttcgtgaa ttttccgaga ttgtctccct actccagccg    480
gtcgcaggtg cacatccggc gattgctcac tttttacaac agcctgatgc cgaacgttta    540
agcgaactgt tcgccagcct gttgaatatg cagggtgaag aaaaatcccg cgcgctggcg    600
attttaaaat cggccctcga tagccagcag ggtgaaccgt ggcaaacgat tcgtttaatt    660
tctgaatttt acccggaaga cagccggtctg ttctccccgc tattgctgaa tgtggtgaaa    720
ttgaaccctg gcgaagcgat gttcctgttc gctgaaacac cgcacgctta cctgcaaggc    780
gtggcgctgg aagtgatggc aaactccgat aacgtgctgc gtgcgggtct gacgcctaaa    840
tacattgata ttccggaact ggttgccaat gtgaaattcg aagccaaacc ggctaaccag    900
ttgttgaccc agccggtgaa acaaggtgca gaactggact cccgattccc agtggatgat    960
```

```
tttgccttct cgctgcatga ccttagtgat aaagaaacca ccattagcca gcagagtgcc      1020
gccattttgt tctgcgtcga aggcgatgca acgttgtgga aaggttctca gcagttacag      1080
cttaaaccgg gtgaatcagc gtttattgcc gccaacgaat caccggtgac tgtcaaaggc      1140
cacggccgtt tagcgcgtgt ttacaacaag ctgtaa                                1176
```

<210> SEQ ID NO 9
<211> LENGTH: 2007
<212> TYPE: DNA
<213> ORGANISM: Artificial Sequence
<220> FEATURE:
<223> OTHER INFORMATION: Known Sequence

<400> SEQUENCE: 9

```
atgggaaaga acagcatcaa actctcagaa ctttggtatt tcaacgagag gaagtggagg        60
tacttcatgg agatagtgaa caaccagaat cagtgcgtgc cttacaattg cttgaacaac       120
cccgaaatcg agatcctcga aggcggaagg atccccgttg gtaataccccc cattgacatt      180 tctctttcac ttactcagtt cctttgagc gagtttgtcc caggtgcggg gttttgtcctt       240 ggcttgatcg acttgatctg gggatttgta ggtccttccc aatgggacgc atttcttgct      300
caagtggagc agttgatcaa ccagaggatc gcagaagctg tcaggaacac agccatccag      360
gaacttgagg aatggcacg ggtttacaga acctatgcta ctgctttcgc tgagtgggaa        420
aaggctcctg atgacccaga gcttcgtgaa gcacttcgta cccaattcac cgcaactgag      480
acttacatca gtggacgcat ctccgttctc aagattcaaa cttttcgaagt acagctgttg     540 tcagtgtttg cccaagctgc caacctccac ttgtctttgc ttagagacgt tgtgttcttt      600
ggtcaaagat ggggtttctc cactaccacc gtgaacaact actacaacga cttgaccgaa      660
ggcattagca cctacaccga ctatgctgtt cgctggtaca taccggact cgaacgtgtt       720 tggggaccgg attctcgtga ttgggtcagg tacaaccagt tcaggagaga gttgaccctc      780
actgtgttgg acatcgttgc tctgtttccg aattacgata gtaggcgcta tcccattcga      840
actgtttccc aactcacacg tgaaatctac acaaacccag tcttggagaa cttcgatggt      900
agtttccgag gctcagctca gggcatgaaa cgtagcatta ggagtccaca cttgatggat      960
atacttaaca gcatcaccat ctataccgat gctcataggg ttactactta tggtcaggt     1020 caccaaatca tggcttctcc tgtcggtttc tcaggtccag agtttacctt tccgctctat     1080
ggaactatgg gaaatgcagc tccacaacaa cgtattgttg cccaactagg tcagggcgtg     1140
tatagaacct tgtcctctac tttctaccgc agacccttca acataggcat caacaaccag     1200
caactctctg ttcttgacgg gacagagttt gcctatggaa cctcctccaa tttgccatcc     1260
gctgtgtaca gaaaaagcgg aactgtagat tccctggatg gatcccacc acagaacaac     1320 aacgtgccac caaggcaagg ctttagccat cgattgagcc atgtttccat gtttcgttca     1380
ggctctagta gcagtgtcag catcataaga gcacctatgt tctcttggat tcatcgtagt     1440
gctgagttca caacatcat tgcatcggat agcattactc aaatccctgc tgtgaaggga     1500
aacttccttt tcaatggttc tgtcatttca ggaccaggat tcactggtgg ggacttagtt     1560
agattgaaca gcagtggaaa taacattcag aatagagggt acattgaagt tcccattcac     1620
tttccatcca catctaccag ataccgagtt cgtgttcggt acgcctctgt taccccgatt     1680
cacctcaacg tcaactgggg taattcctcc attttctcca acacagttcc agctactgct     1740
acctcccttg acaacctaca atctagcgac ttcggttact tcgagagcgc caacgccttc     1800
acatcttcac ttggtaatat cgttggtgtt agaaatttca gtgggactgc tggagtgatc     1860
```

```
atagacagat tcgagttcat tcccgttact gcaacacttg aggctgagta caacctggaa    1920
agagcccaga aggccgtgaa tgccctgttt acctctacaa accagctagg gctcaagacc    1980
aatgtcactg actaccacat tgattga                                        2007
```

```
<210> SEQ ID NO 10
<211> LENGTH: 18
<212> TYPE: DNA
<213> ORGANISM: Artificial Sequence
<220> FEATURE:
<223> OTHER INFORMATION: Primer 1

<400> SEQUENCE: 10
tcatttgggg cttcgtcg                                                  18

<210> SEQ ID NO 11
<211> LENGTH: 22
<212> TYPE: DNA
<213> ORGANISM: Artificial Sequence
<220> FEATURE:
<223> OTHER INFORMATION: Primer 2

<400> SEQUENCE: 11
tgattgatca gctgctcaac ct                                             22

<210> SEQ ID NO 12
<211> LENGTH: 23
<212> TYPE: DNA
<213> ORGANISM: Artificial Sequence
<220> FEATURE:
<223> OTHER INFORMATION: Probe 1

<400> SEQUENCE: 12
ccagtgggat gcgttcctcg ctc                                            23

<210> SEQ ID NO 13
<211> LENGTH: 22
<212> TYPE: DNA
<213> ORGANISM: Artificial Sequence
<220> FEATURE:
<223> OTHER INFORMATION: Primer 3

<400> SEQUENCE: 13
cgactatgct gttcgctggt ac                                             22

<210> SEQ ID NO 14
<211> LENGTH: 23
<212> TYPE: DNA
<213> ORGANISM: Artificial Sequence
<220> FEATURE:
<223> OTHER INFORMATION: Primer 4

<400> SEQUENCE: 14
gttgtacctg acccaatcac gag                                            23

<210> SEQ ID NO 15
<211> LENGTH: 24
<212> TYPE: DNA
<213> ORGANISM: Artificial Sequence
<220> FEATURE:
<223> OTHER INFORMATION: Probe 2

<400> SEQUENCE: 15
cggtccccaa acacgttcga gtcc                                           24
```